US009504420B2

(12) United States Patent
Davis et al.

(10) Patent No.: US 9,504,420 B2
(45) Date of Patent: Nov. 29, 2016

(54) METHODS AND ARRANGEMENTS FOR IDENTIFYING DERMATOLOGICAL DIAGNOSES WITH CLINICALLY NEGLIGIBLE PROBABILITIES

(71) Applicant: Digimarc Corporation, Beaverton, OR (US)

(72) Inventors: Bruce L. Davis, Lake Oswego, OR (US); Tony F. Rodriguez, Portland, OR (US); John Stach, Portland, OR (US)

(73) Assignee: Digimarc Corporation, Beaverton, OR (US)

( * ) Notice: Subject to any disclaimer, the term of this patent is extended or adjusted under 35 U.S.C. 154(b) by 171 days.

(21) Appl. No.: 14/289,493

(22) Filed: May 28, 2014

(65) Prior Publication Data

US 2015/0003699 A1  Jan. 1, 2015

Related U.S. Application Data

(60) Division of application No. 14/276,578, filed on May 13, 2014, which is a continuation of application No. PCT/US2014/034706, filed on Apr. 18, 2014, and a (Continued)

(51) Int. Cl.
*G06F 9/00* (2006.01)
*A61B 5/00* (2006.01)
(Continued)

(52) U.S. Cl.
CPC ............. *A61B 5/441* (2013.01); *A61B 5/0075* (2013.01); *A61B 5/0077* (2013.01); *A61B 5/1034* (2013.01); *A61B 5/444* (2013.01); *A61B 5/445* (2013.01); *A61B 5/6898* (2013.01); *A61B 5/7246* (2013.01); *A61B 5/7278* (2013.01);

(Continued)

(58) Field of Classification Search
None
See application file for complete search history.

(56) References Cited

U.S. PATENT DOCUMENTS

2006/0210132 A1  9/2006  Christiansen, II et al.
2009/0190812 A1  7/2009  Sano et al.
(Continued)

FOREIGN PATENT DOCUMENTS

WO  WO2011135573  11/2011

OTHER PUBLICATIONS

PCT International Search Report and the Written Opinion of the International Searching Authority, PCT/US2014/034706, mailed Sep. 2, 2014.

*Primary Examiner* — Weiwen Yang
(74) *Attorney, Agent, or Firm* — Digimarc Corporation

(57) ABSTRACT

Reference imagery of dermatological conditions is compiled in a crowd-sourced database (contributed by clinicians and/or the lay public), together with associated diagnosis information. A user later submits a query image to the system (e.g., captured with a smartphone). Image-based derivatives for the query image are determined (e.g., color histograms, FFT-based metrics, etc.), and are compared against similar derivatives computed from the reference imagery. This comparison identifies diseases that are not consistent with the query image, and such information is reported to the user. Depending on the size of the database, and the specificity of the data, 90% or more of candidate conditions may be effectively ruled-out, possibly sparing the user from expensive and painful biopsy procedures, and granting some peace of mind (e.g., knowledge that an emerging pattern of small lesions on a forearm is probably not caused by shingles, bedbugs, malaria or AIDS). A great number of other features and arrangements are also detailed.

9 Claims, 6 Drawing Sheets

Related U.S. Application Data continuation-in-part of application No. 14/206,109, filed on Mar. 12, 2014.

(60) Provisional application No. 61/978,632, filed on Apr. 11, 2014, provisional application No. 61/813,295, filed on Apr. 18, 2013, provisional application No. 61/832,715, filed on Jun. 7, 2013, provisional application No. 61/836,560, filed on Jun. 18, 2013, provisional application No. 61/872,494, filed on Aug. 30, 2013.

(51) Int. Cl.
| | | |
|---|---|---|
| *G06F 19/00* | (2011.01) | |
| *G06T 5/40* | (2006.01) | |
| *G06T 7/00* | (2006.01) | |
| *G06T 7/40* | (2006.01) | |
| *A61B 5/103* | (2006.01) | |
| *G06F 17/30* | (2006.01) | |
| *G10L 19/018* | (2013.01) | |

(52) U.S. Cl.
CPC ............ *A61B 5/743* (2013.01); *A61B 5/7425* (2013.01); *A61B 5/7485* (2013.01); *G06F 17/30424* (2013.01); *G06F 17/30554* (2013.01); *G06F 19/345* (2013.01); *G06F 19/3418* (2013.01); *G06F 19/3443* (2013.01); *G06T 5/40* (2013.01); *G06T 7/0012* (2013.01); *G06T 7/408* (2013.01); *G10L 19/018* (2013.01); *A61B 5/4806* (2013.01); *A61B 5/7282* (2013.01); *A61B 2576/02* (2013.01); *G06T 2207/30088* (2013.01)

(56) References Cited

U.S. PATENT DOCUMENTS

| | | | |
|---|---|---|---|
| 2009/0304243 | A1 | 12/2009 | Mertz et al. |
| 2012/0008838 | A1* | 1/2012 | Guyon .................. G06F 19/345 382/128 |
| 2012/0077696 | A1 | 3/2012 | Admon et al. |
| 2013/0322711 | A1* | 12/2013 | Schultz ............... G06F 19/3418 382/128 |

\* cited by examiner

| IMAGE(S) | IMAGE DERIVATIVES | LOCATION | DIAGNOSIS | OTHER METADATA |
|---|---|---|---|---|
| ... | ... | ... | ... | ... |
| 56F8E21.TIF | 56F8E21_HIST(1,1).DAT<br>56F8E21_HIST(1,2).DAT<br>...<br>56F8E21_FFT(1,1).DAT<br>56F8E21_FFT(1,2).DAT<br>... | BACK | <DIAG>TINEA VERSICOLOR</DIAG> | <AGE>54</AGE><br><GENDER>M</GENDER><br><WEIGHT>230</WEIGHT><br><ZIP>97221</ZIP><br><DRUG>ATENOLOL</DRUG><br><DRUG>VITAMIN_A</DRUG><br><MED>HYPERTENSION</MED/... |
| 56F8E22.TIF | 56F8E22_HIST(1,1).DAT<br>56F8E22_HIST(1,2).DAT<br>...<br>56F8E22_FFT(1,1).DAT<br>56F8E22_FFT(1,2).DAT<br>... | ARM | <DIAG>PITYRIASIS ROSEA</DIAG> | <AGE>37</AGE><br><GENDER>F</GENDER><br><ZIP>07974</ZIP><br><DIET>ALMOND_MILK</DIET><br><DRUG>AMOXYCILLIN</DRUG><br><DRUG>FLUTICASONE</DRUG><br><TRIP>GUATEMALA</TRIP>... |
| 56F8E23.TIF | 56F8E23_HIST(1,1).DAT<br>56F8E23_HIST(1,2).DAT<br>...<br>56F8E23_FFT(1,1).DAT<br>56F8E23_FFT(1,2).DAT<br>... | LEG | | <LIFE>RUNNER</LIFE><br><LIFE>SWIMMER</LIFE><br><DRUG>ALPRAZOLAM</DRUG> |
| 56F8E24A.TIF<br>56F8E24B.TIF | 56F8E24A_HIST(1,1).DAT<br>56F8E24A_HIST(1,2).DAT<br>...<br>56F8E24B_FFT(1,1).DAT<br>56F8E24B_FFT(1,2).DAT<br>... | FACE | | <AGE>48</AGE><br><LIFE>OUTDOOR WORKER</LIFE><br><MED>DIABETES</MED><br><FAMILY>MELANOMA</FAMILY> |
| ... | ... | ... | ... | ... |

FIG. 2

FIG. 3A
FIG. 3B
FIG. 4
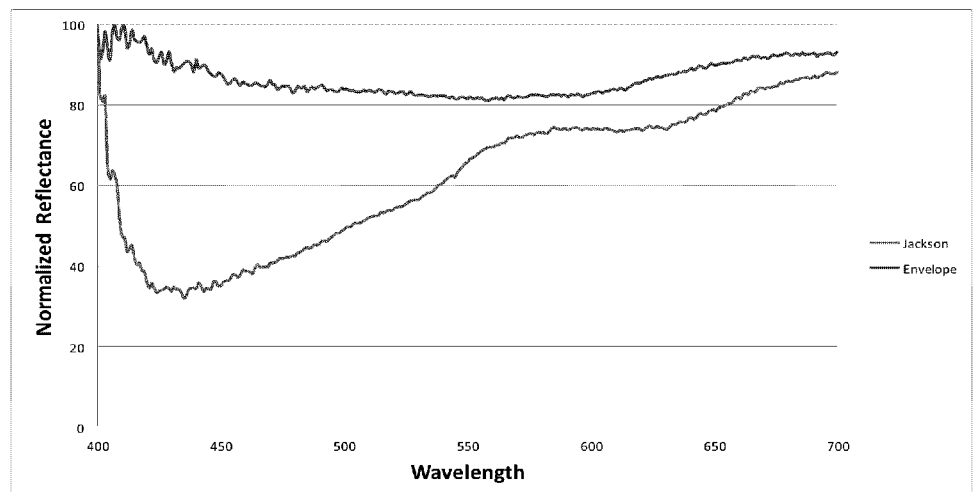

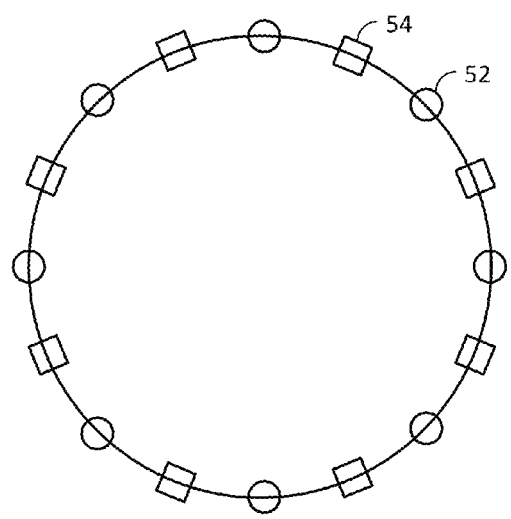
FIG. 5
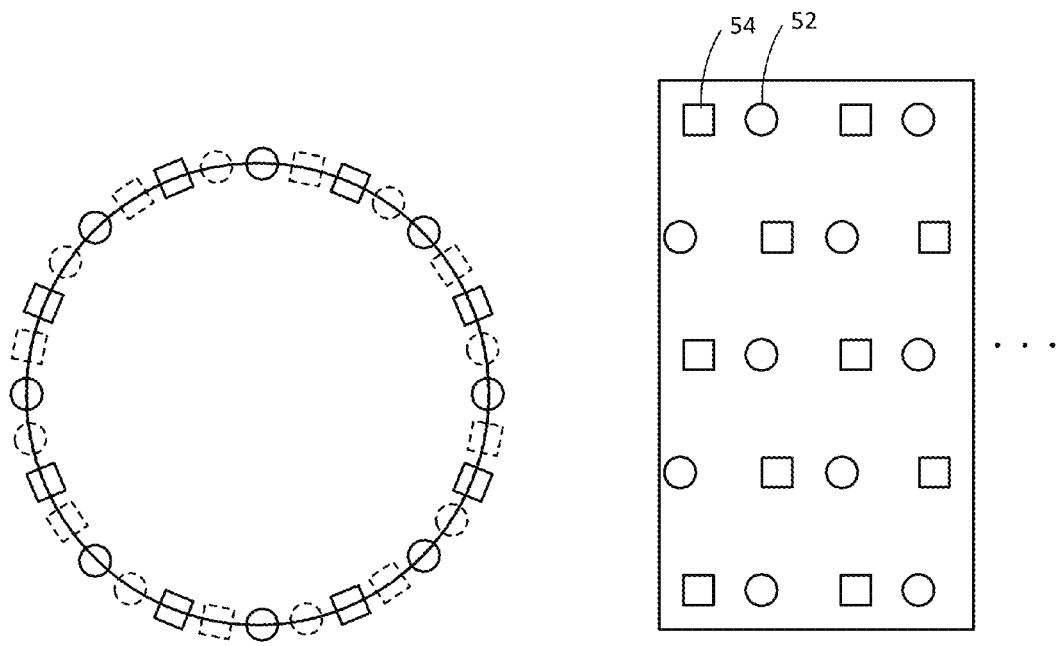
FIG. 6A  FIG. 6B

METHODS AND ARRANGEMENTS FOR IDENTIFYING DERMATOLOGICAL DIAGNOSES WITH CLINICALLY NEGLIGIBLE PROBABILITIES

RELATED APPLICATION DATA

This application is a division of application Ser. No. 14/276,578, filed May 13, 2014 (published as 20140378810), which is a continuation of international application PCT/US14/34706, filed Apr. 18, 2014 (published as WO2014172671), which claims priority to provisional application 61/978,632, filed Apr. 11, 2014. This application is also a continuation-in-part of application Ser. No. 14/206,109, filed Mar. 12, 2014 (published as 20140316235), which claims priority to provisional applications 61/813,295, filed Apr. 18, 2013; 61/832,715, filed Jun. 7, 2013; 61/836,560, filed Jun. 18, 2013; and 61/872,494, filed Aug. 30, 2013. These applications are incorporated herein by reference.

INTRODUCTION

Medical diagnosis is an uncertain art, which depends largely on the skill and experience of the practitioner. For example, dermatological diagnosis tends to be based on very casual techniques, like observation by doctor, or on very invasive techniques, like biopsies. Skin condition degrades with age. It is difficult for people to differentiate the effects of normal aging from disease. This leads to lots of worry and unnecessary doctor visits. More rigorous diagnostic techniques can be applied to educate the public, assist medical professionals, and lower health care costs.

An example is diagnosis of diseases evidenced by skin rashes and other dermatological symptoms. A skilled dermatologist may be able to accurately identify dozens of obscure conditions by their appearance, whereas a general practitioner may find even some common rashes to be confounding. But highly skilled practitioners are sometimes puzzled, e.g., when a rash appears on a traveler recently returned from the tropics, and the practitioner has no experience with tropical medicine.

Some of the dimensions of differential diagnosis in dermatology include location on body, color, texture, shape, and distribution. Other relevant factors include age, race, sex, family tree, and geography of person; and environmental factors including diet, medications, exposure to sun, and occupation. Many skin conditions have topologies and geographies that can be mapped in various dimensions, including depth, color and texture.

The prior art includes smartphone apps that are said to be useful in diagnosing skin cancer. Some rely on computerized image analysis. Others refer smartphone snapshots to a nurse or physician for review. The former have been found to perform very poorly. See, e.g., Wolf et al, Diagnostic Inaccuracy of Smartphone Applications for Melanoma Detection, JAMA Dermatology, Vol. 149, No. 4, April 2013 (attached to application 61/872,494).

In accordance with one embodiment of the present technology, imagery of dermatological conditions and other enrollment information is compiled in a crowd-sourced database, together with associated diagnosis information. This reference information may be contributed by physicians and other medical personnel, but can also be provided by the lay public (e.g., relaying a diagnosis provided by a doctor).

A user submits a query image to the system (typically with anonymous enrollment/contextual information, such as age, gender, location, and possibly medical history, etc.). Image-based derivatives are determined (e.g., color histograms, FFT-based metrics, etc.) for the query image, and are compared against similar derivatives for the reference imagery. In one arrangement, those reference images whose derivatives most closely correspond to the query image are determined, and their associated diagnoses are identified. This information is presented to the user in a ranked listing of possible pathologies. In some embodiments, when the user's submitted query image and associated information is analyzed by the system and several likely diagnoses identified, the system may provide specific questions (guided by the results of the current analysis) to the user, or requests for additional images, to help distinguish among the candidate diagnoses.

In a variant arrangement, the analysis identifies diseases that are not consistent with the query image and associated information. Again, this information is reported to the user (expressly; not simply by omission) and may include a risk profile that conveys statistical and/or qualitative measures of risk about such information.

In some embodiments, the imagery is supplemented with 3D information about the surface topology of the skin, and this information is used in the matching process. Such 3D information can be derived from the imagery, or may be separately sensed.

Depending on the specificity of the data, and the size of the crowd-sourced database, 90%, 98%, or more of candidate conditions can be effectively ruled-out through such methods. A professional using such technology may thus be able to spare a patient expensive and painful testing (e.g., biopsies), because the tested-for conditions can be reliably screened by reference to the large corpus of reference imagery and associated knowledge generated by the system. Similarly, a worried user may be relieved to quickly learn, for example, that an emerging pattern of small lesions on a forearm is probably not caused by shingles, bedbugs, malaria or AIDs.

In some embodiments, the knowledge base includes profile information about the subjects whose skin conditions are depicted. This profile information can include, e.g., drugs they are taking, places they have visited in the days leading up to onset of symptoms, medical history, lifestyle habits, etc. When a user submits a query image, and the system identifies reference imagery having matching derivatives, the system can also report statistically-significant co-occurrence information derived from the profile information. For example, the system may report that 27% of people having a skin condition like that depicted in the user's query image report taking vitamin A supplements.

In some embodiments, the co-occurrence information is broken down by candidate diagnoses. For example, the system may report that the top candidate diagnosis is miliaria X (42% chance). 35% of people with this diagnosis report having been in the tropics in the 30 days prior to onset of symptoms, and 25% report occasional use of hot tubs or saunas. The next top candidate diagnosis is tinea Y (28% chance). 60% of people with this diagnosis report having chicken pox as a child. Such co-occurrence information can help in making a differential diagnosis from among the offered alternatives.

Sometimes a patient is less concerned with the diagnosis than simply wanting to be rid of an affliction. Thus, some embodiments of the technology do not attempt to identify, or rule-out, particular diagnoses. Instead, they simply seek to identify correlated factors from the knowledge base created from information from users, image analysis, and crowd-sourced data, so that possibly causative factors might be addressed (e.g., by suspending intake of supplemental vitamin A, in the example given above).

Typically, the user-submitted information is added to the knowledge base, and forms part of the reference information against which future submissions are analyzed.

While described primarily in the context of skin imagery, the principles of the present technology are likewise applicable with any physiologically-derived signals. An example is audio. Audio signals include heart sounds and other cardiovascular sounds (including murmurs, bruits, and other blood flow noises), lung and other respiratory sounds (including crackles, rales, rhonchi, wheezes, coughs, snoring and other air flow noises), bowel and digestive sounds, joint noises (e.g., pops and creaks), as well as speech and other vocalizations.

The foregoing and other features and advantages of the present technology will be more readily apparent from the following detailed description, which proceeds with reference to the accompanying figures.

BRIEF DESCRIPTION OF THE DRAWINGS

FIG. 2 illustrates conceptual organization of an exemplary diagnostic system using technology disclosed herein.

FIG. 3A shows a banknote, and FIG. 3B shows an excerpt from the banknote.

FIG. 4 shows normalized reflectance plots for the FIG. 3B banknote excerpt, and for a white envelope.

FIG. 5 is a schematic sectional view of a full-body imaging booth.

FIGS. 6A and 6B are views depicting features of alternate imaging booths.

DETAILED DESCRIPTION

Figure 1:
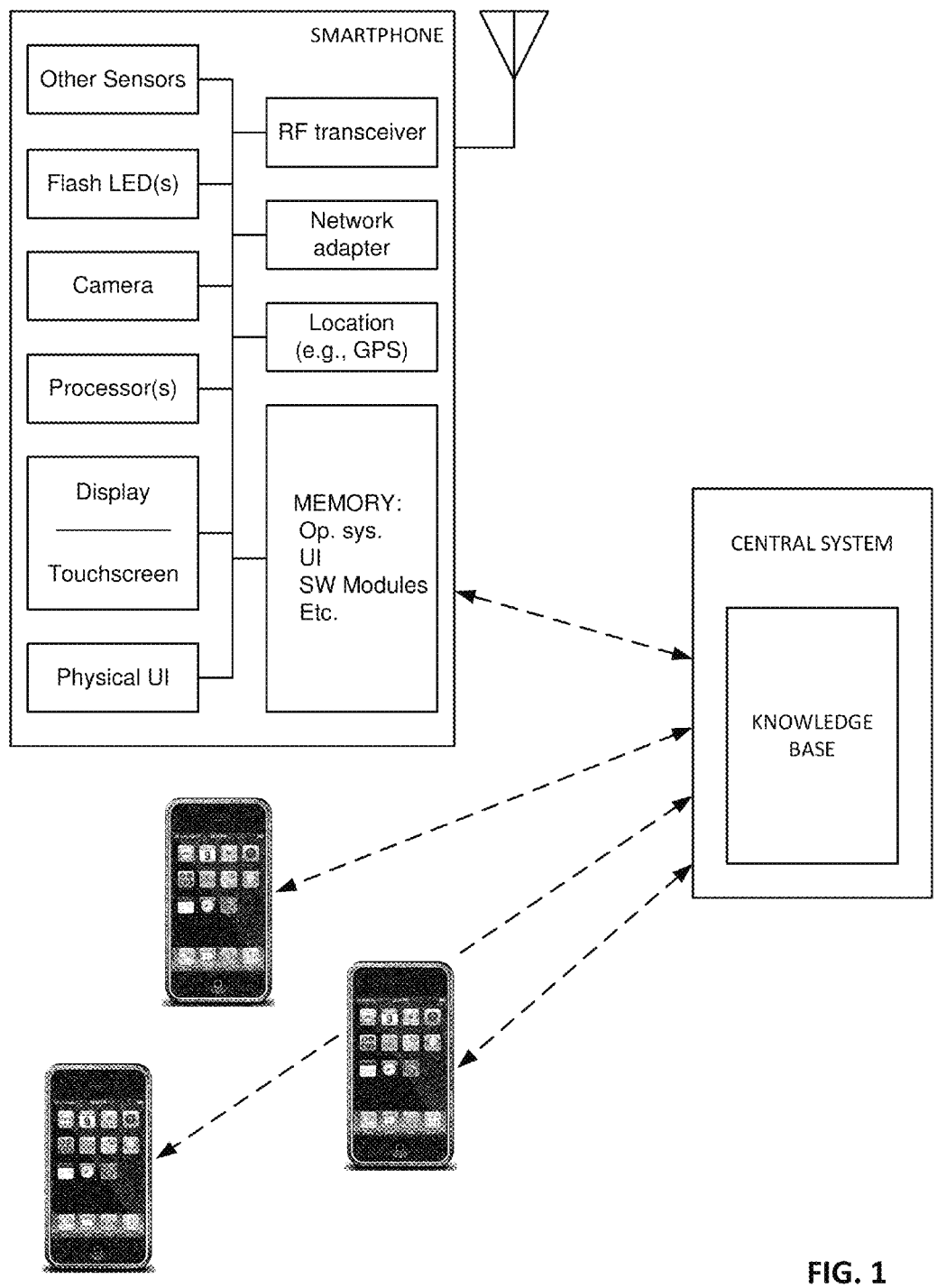
FIG. 1 illustrates components of one implementation of the technology, including plural remote terminals (e.g., smartphones), and one or more central systems.

FIG. 1 shows a hardware overview of one embodiment employing principles of the present technology. Included are one or more user terminals (e.g., smartphones), and a central system.

As is familiar, each smartphone includes various functional modules—shown in rectangles. These include one or more processors, a memory, a camera, and a flash. These latter two elements are controlled by the processor in accordance with operating system software and application software stored in the memory.

The central system similarly includes one or more processors, a memory, and other conventional components. Particularly shown in FIG. 1 is a knowledge base—a database data structure that facilitates storage and retrieval of data used in the present methods.

One aspect of the present technology includes the central system receiving first imagery depicting a part of a human body that evidences a symptom of a pathological condition (e.g., skin rash or bumps). This imagery (and its image metadata) can be uploaded to the central system from one of the user terminals using commonly available image submission means and enrollment. The image then is processed to derive one or more image parameter(s). A data structure containing reference information is then searched, for reference image data that is parametrically similar to the first imagery. Based on results of this search, one or more particular pathological conditions that are not the pathological condition evidenced by the depicted part of the human body are identified. Resulting information is then communicated to the originating user terminal.

In some cases, it may be useful to present "similar" images to the user, along with any accompanying diagnoses. In these cases, it is important to ensure that the presented images are relevant to the user. In many implementations, a machine learning approach will be suitable for determining candidate diagnoses. Many features, whether part of the raw user images, or processed versions thereof, are presented to the machine learning algorithm. Additional features, representing age, gender, race, height, weight, etc., are also likely to be input to the algorithm. The machine learning algorithm can output a set of candidate diagnoses which best match the user's images and additional information. If representative images are to be presented to the user as representative of their diagnoses, the images should be chosen from the database not just based upon visual similarity, but also based upon how well the database image's associated additional features (age, gender, etc.) match the user.

(For expository convenience, the terms image, imagery, image data, and similar words/expressions, are used to encompass traditional spatial luminance/chrominance representations of a scene, and also to encompass other information optically captured from a subject. This can include, for instance, 3D microtopology. Such terms also encompass such information represented in non-spatial domains, e.g., FFT data, which represents the information is a spectral domain.)

The derived image parameter(s) can be of various types, with some types being more discriminative for some pathologies, while other types are more discriminative for others.

One sample derived image parameter is a color histogram. This histogram may be normalized by reference to a "normal" skin color, e.g., as sampled from a periphery of the area exhibiting the symptom.

Particular types of suitable color histograms are detailed in Digimarc's U.S. Pat. No. 8,004,576. One such histogram is a 3D histogram, in which the first and second histogram dimensions are quantized hues (e.g., red-green, and blue-yellow), and the third histogram dimension is a quantized second derivative of luminance.

Desirably, the imagery is spectrally accurate, so that hue-based image derivatives are diagnostically useful. One low cost approach to acquiring such imagery is by gathering multiple frames of imagery under different, spectrally tuned illumination conditions, and processing same, as detailed in co-pending application Ser. No. 13/840,451, filed Mar. 15, 2013 (now published as 20130308045), and Ser. No. 14/201,852, filed Mar. 8, 2014 (now published as 20140293091)

Another type of derived image parameter is a transformation of the imagery into a spatial frequency domain representation (e.g., FFT data). Such representation decomposes the image into components of different frequencies, angular orientations, phases and magnitudes (depending on the manner of representation). Parameters of this type are particularly useful in discerning skin textures, which are often useful as diagnostic criteria. The decomposition of the image into such spatial frequency components can be conducted separately in different channels, e.g., yielding two-, three- or more-binned representations of different image chrominance and luminance planes. (More than the usual tri-color image representations can be used. For example, the image may be represented with 4-20 different color channels.)

Still another image derivative is wavelet transform data. Such information is again a decomposition of the image information into a collection of orthonormal basis functions—in this case wavelets.

A variety of other domain transformations can similarly be applied to the imagery to serve as the basis of image metrics for matching.

Yet another image derivative is blob analysis. One form of such analysis involves "region growing." A particular method, practiced in the pixel domain, involves selecting a seed pixel, and adding to a blob all of the contiguous pixels whose values are within a threshold value range of the seed pixel, e.g., plus or minus three digital numbers in luminance, on a 0-255 scale. This process can be repeated for seed pixels throughout the image. The seed pixels can be selected based on color or other parameter (e.g., a local maxima in image redness or contrast), or may be chosen randomly. What results is a pattern of 2D regions whose shape and scale parameters are useful as diagnostic indicia.

A particular image metric derived from blob analysis is a histogram identifying frequency of occurrence of different shapes. Shapes may be classified in various fashions. A simple two-class division, for example, may distinguish shapes that have exclusively convex boundaries (e.g., circles and ovoids) from shapes that have a concave aspect to part of their peripheries (e.g., blobs that have one or more inwardly-directed dimples). Much more sophisticated techniques are commonly used in blob analysis; an example is a histogram of oriented gradients. (See, e.g., Dalal, et al, Histograms of Oriented Gradients for Human Detection, IEEE Conference on Computer Vision and Pattern Recognition, pp. 886-893, 2005.)

(Commonly, such blob analysis is performed using a support vector machine method, which classifies shapes based on a set of reference training data.)

While luminance was used in the foregoing example, the technique can also be practiced in a particular color channel, or in Boolean logical combinations of color channels (e.g., add to the blob region those pixels whose value in a 500 nm spectral band is within 3 digital numbers of the seed value, OR whose value in a 530 nm spectral band is within 5 digital numbers of the seed value).

Similar methods can be practiced in other domains, such as using a representation of imagery in the spatial frequency domain.

All such image derivatives (metrics) can be computed on different scales. One scale is across the totality of an image. Another is to divide the image into hundreds of portions, and compute the metrics for each such portion. The same image can be re-divided into tens of thousands of portions, with the metrics again recomputed. These portions may be of any shape; rectangular is often computationally efficient, but others can be used. The portions may be disjoint, tiled, or overlap. If computational constraints require, the finer scale metrics can be computed on a subset of all such regions, such as on a random selection of 1% of 100,000 regions.

As indicated, the image derivatives can be computed on different color channels. Using methods detailed in the pending patent application Ser. No. 13/840,451 (now published as 20130308045) and Ser. No. 14/201,852, for example, an image can be captured and accurately decomposed into five or ten or more different spectral bands—each of which may have diagnostic utility. Such spectral-based analysis is not limited to the visible spectrum; infrared and ultraviolet data is also useful.

(Ultraviolet light is absorbed by melanin. Thus, illumination with UV can reveal irregular pigment distribution, which can aid, e.g., in defining the borders of melanoma.)

(The CMOS and CCD sensors used in conventional digital cameras are typically responsive well into the infrared, provided there is no IR filtering.)

The image, and image derivatives, can also be based on polarized light photography.

Bag-of-features techniques can be applied to the image derivatives, e.g., as detailed in Csurka, et al, Visual Categorization with Bags of Keypoints, ECCV, Workshop on Statistical Learning in Computer Vision, 2004.

Another image derivative is feature size. Dimensions (e.g., diameter) of lesions and other visually-distinguishable skin features can be assessed from imagery, and this data included with the derivative image data. (The diagnostic profile of a feature is often dependent on its size.)

FIG. 2 is an excerpt of a conceptual view of a reference database. It includes a variety of records (rows), each comprising a set of data relating to a reference subject.

The first column contains an image (or a set of images) depicting a dermatological condition of the subject. An image can comprise, e.g., a 10 megabyte color TIF file.

The second column shows some of the image derivatives computed from the image. The naming convention gives semantic information about the type of data, e.g., indicating whether it is histogram or FFT data, and the coordinate of a tiled sub-region of the image from which the data was derived.

The third column shows the location on the subject's body from which the image was captured.

The fourth column shows, if available, a diagnosis of the reference subject's affliction. For some entries, no diagnosis is provided.

The fifth column shows additional user metadata. Examples include demographic information (e.g., age, gender, weight, height, race, residence location by zip code), and other profile data about the subject. This can include drugs taken in the past thirty days, any on-going medical conditions, foods introduced into the subject's diet in the past thirty days, travel within the past sixty days, lifestyle activities, environmental exposures, family medical history, etc.

It will be seen that information in the fourth and fifth columns is tagged using XML-style descriptors, to provide for extensibility and to facilitate text parsing.

A query image submitted by the user can similarly be accompanied by the body location and other user metadata information shown in FIG. 2.

(Not shown in FIG. 2, but typically present in the knowledge base for each image, is metadata concerning the image capture parameters, e.g., in the standard EXIF format.)

In an illustrative embodiment, a server system determines similarity scores between a query image and each of many reference images. One component of such a score can be based on the reciprocal of a Euclidean distance between an image derivative from the query image and a corresponding image derivative for a reference image, in the image derivative feature space. Since each image may have thousands of derivatives (e.g., based on different regions and color channels), there can be many thousands of such components (e.g., comparing a histogram of region 1 of the query image with histograms of regions 1-1,000 of a reference image, and likewise for region 2 of the query image, etc.). Typically, such feature similarity metrics that fall below a statistically significant threshold are ignored.

In computing a similarity score for a reference image (i.e., relative to a query image), some image derivatives are weighted more heavily than others. For example, the weight given to a particular correspondence between a pair of image derivatives can depend on the scale of the portions between which similarity was found. The larger the feature, the more weight is typically given (e.g., in linear or exponential proportion to feature size). Similarly, some indicia are more diagnostically relevant than others. Spectral data at 500 nm may be more discriminative than spectral data at 700 nm, and may be given a commensurately greater weight, etc. Weightings can be calculated recursively, accounting for feedback from users of the system about correlations.

A sampling, or all, of the reference images in the database are thus scored relative to the query image. In an illustrative embodiment, the reference images that are scored in the top 5%, or 0.5%, of the universe of evaluated reference images are thereby identified. Associated user metadata for this set of reference images is then analyzed.

Naturally, many of the top matches will be errant. Some of the information in the database may also be incorrect. In an information theoretic sense, the data will be very noisy. But in the aggregate, over a large data set, statistically significant and useful correlations will be evident.

For example, analysis of the top-scoring set of reference images may find that 40% are associated with diagnostic tags indicating that they depict the condition known as tinea versicolor, and 23% may be similarly tagged as depicting pityriasis rosea. 25% of the top-scoring reference images may be associated with diagnostic tags indicating that the reference subject was taking the blood pressure medicine Atenolol.

Of course, a person either has a condition, or doesn't. A person doesn't suffer from "40% tinea versicolor, 23% pityriasis rosea, etc." But such a ranked presentation of candidates provides specific hypotheses that can then be further investigated.

A statistical breakdown of such correlations is typically provided to the user—in one or more rank-ordered sets. For example, the user may be presented with a rank-ordered listing of the top five or ten possible diagnoses—each including a stated probability based on frequency of occurrence from the top-matching reference image set. Similar listings may be presented for demographic information and other profile data (e.g., drug correlations, diet correlations, lifestyle correlations, etc.).

It will be understood that many skin conditions are themselves symptoms of non-skin disorders. A familiar example is skin jaundice, which may be associated with liver failure. Such non-skin diagnoses should also be reflected in the knowledge base, and in the results reported to the user.

The absence of apparent correlation can additionally, or alternatively, be reported to the user. If less than 0.03% of the reference images in the top-scoring set are associated with tinea versicolor, whereas this condition has a much greater frequency of occurrence in the full reference image set (e.g., 1.5%), then the user can be informed that the skin condition is most likely not tinea versicolor. Likewise with drugs, diet, lifestyle, etc. (The particular threshold used in such evaluation can be determined empirically.)

The information presented to the user can also include samples of closely-matching reference imagery—and the diagnosis (if any) associated with each.

Another method makes use of changes in the user's depicted symptoms over time. In such a method, the user submits two images to the system—an initial one, and a second one taken at a later time. The system determines data about a change in the depicted skin symptom between these two times based on the submitted imagery. This determined data is then used in further refining diagnostic information.

Thus, for example, if purpura on the skin enlarge in size during the course of a disease, this is evidence in favor of certain candidate diagnoses, and contrary to other candidate diagnoses. Three or more time-based images can likewise be used.

Crowd-sourced data gathering, with subsequent scoring and statistical calculations as described herein, should both be initiated as well as managed as it evolves. Expert medical practitioners have the opportunity to "seed" such databases with known imagery examples of a variety of afflictions, paying a great deal of attention to ensuring a wide range of angles, lighting conditions, parts of the body, camera models, etc. This can involve the submission of hundreds, thousands or even more images with clinically derived examples of the major and less major categories of affliction. Likewise, even as the crowd sourced imagery grows with time and may soon wind up dwarfing any original "ground truth" imagery, expert practitioners can still submit known examples of afflictions into the up-to-date crowd-sourced service as described, witness the results of the returned information, then proceed to tune or modify various weighting factors, scoring approaches, extensions to XML fields, etc., thereby managing the diagnostic accuracy of the overall service as more and more clients begin to use the service.

It will be recognized that certain embodiments of this technology differ from earlier crowd-sourced dermatological efforts in various ways. For example, some of the earlier work compiled a crowd-sourced collection of images that were each accompanied by professional diagnosis data. The illustrative embodiment has no such requirement. Similarly, other earlier work employed a "crowd" to offer plural human assessments of submitted images, from which a consensus conclusion was derived. The illustrative embodiments do not require such plural human assessments.

Unprecedented knowledge will be revealed as the present system grows to large scale. Error tends towards zero as the universe of data grows large.

Data Capture

The capturing of data from skin can employ known and forthcoming imaging technologies. A simple one is a smartphone camera. Accessory optics may be employed to provide better close-up capabilities. Other digital cameras—including those on headworn devices—can also be used.

Exemplary smartphones include the Apple iPhone 5; smartphones following Google's Android specification (e.g., the Galaxy S5 phone, manufactured by Samsung, and the Google Moto X phone, made by Motorola), and Windows 8 mobile phones (e.g., the Nokia Lumia 1020, which features a 41 megapixel camera).

Some embodiments employ modular mobile device technology, such as Google's Project Ara (which derives from the Phonebloks concept developed by Dave Hakkens; see, e.g., YouTube video oDAw7vW7H0c and the phonebloks<dot>com web site). In such arrangements, a mobile device is comprised of detachable components, which can be added, changed or upgraded as needs dictate. Through such technologies, a device can be assembled that includes sensors of the sorts detailed in this disclosure, especially adapted for physiologic data capture.

Imagery employed in the present technology may be in JPEG format, but preferably is in a higher quality form—such as RAW or TIF.

The smartphone or other user device can compute some or all of the derivative information from the sensed data before sending data to the remote database, or the central system can perform such calculations, based on provided sensor data. Or these tasks can be distributed—part performed on one platform, and part on another.

In addition to smartphone cameras, image capture can employ purpose-built hardware. Examples are disclosed in patent publication 20110301441. Commercial products include the Dermograph imager by MySkin, Inc., and the Handyscope by FotoFinder Systems. The latter is an accessory for the Apple iPhone 5 device and includes built-in illumination—optionally cross-polarized. It is capable of capturing both contact images (with the device touching the skin), and non-contact images. A variety of other dermatoscopy (aka epiluminescence microscopy) hardware systems are known.

In some arrangements, a physical fixture can be provided on the imaging device to help establish a consistent imaging distance to the skin. A rigid black, white or clear plastic cowl, for example, can extend from the camera lens (and optionally flash) at one end, to an opening that is placed over the skin, for controlled-distance imaging.

Software on the smartphone may employ known autofocus technology to set an initial image focus, and can warn the user if the camera is unable to achieve proper focus. However, some auto-focus algorithms are easily fooled into focusing on dark hair that may rise above the skin surface. Accordingly, it is preferable to capture several still image exposures—one at the nominal auto-focus setting, and others that are varied under software control from that position, e.g., at focal planes plus and minus two and four millimeters from the auto-focus setting. Known computational photography techniques can combine such images to yield a composite image with an extended depth of field, as detailed, e.g., in Jacobs et al, Focal Stack Compositing for Depth of Field Control, Stanford Computer Graphics Laboratory Technical Report 2012-1, attached to application 61/872,494. (Other extended depth of field technologies can also be employed, e.g., as detailed in U.S. Pat. Nos. 7,218,448, 7,031,054 and 5,748,371.)

Similarly, the software can employ exposure-bracketing, since some features may more easily be distinguished in exposures taken one or two f-stops above, or below, an autoexposure setting. Known high dynamic range methods can be employed to composite such images into an enhanced image frame.

In some arrangements, a camera's frame capture is triggered based on stability. A stability metric can be based on data from a smartphone sensor (e.g., an accelerometer). Or it can be based on analysis of the viewfinder image data. (The Apple iPhone device includes motion estimation hardware, which is most commonly employed for MPEG video compression, but which also can track features in an image frame to assess image stability.)

While imagery captured by mobile cameras is a focus of this disclosure, it will be recognized that imagery captured by whole body scanning systems can likewise be employed. Canfield Scientific is among the commercial providers of whole body scanners.

In between smartphones and whole-body scanners are a range of intermediate imaging systems. One is an automated apparatus that might be found in a doctor's office or pharmacy, which serves to capture imagery from a user and submit it to the central system for analysis, as detailed herein. Such apparatus (which may be, e.g., a stand-alone kiosk, or integrated into a weight scale in a doctor's office—capturing frontal face and neck imagery each time a patient is weighed) can be more sophisticated than that found in most smartphones, e.g., providing controlled spectral illumination (e.g., as in application Ser. No. 13/840,451 (now published as 20130308045) and Ser. No. 14/201,852), thermal imaging, etc. It may provide the user with a hardcopy printout of the results. Such an apparatus may be available for free use, or a nominal charge may be collected (e.g., by coin, dollar, or credit card).

As is familiar to artisans, various photosensitizers (e.g., aminolevulinic acid) can be applied to the skin, to highlight certain tumors, etc., such as by changing their absorbance and fluorescence spectra.

In some methods, the user moves a smartphone over a body area, while the camera captures imagery multiple frames of imagery. From the different viewpoint perspectives, 3D information about the skin's surface relief (topology) is discerned, e.g., using familiar stereoscopy techniques. Google's patent publication 20130201301 details one such arrangement for creating 3D imagery from smartphone images captured at different viewpoints. Known Simultaneous Localization and Mapping (SLAM) and Structure from Motion (SFM) techniques can also be employed—revealing scale as well as shape. Such a 3D data representation can be virtually flattened, using cartographic techniques, for analysis and rendering to the user.

Patent application Ser. No. 13/842,282, filed Mar. 15, 2013 (published as 20140198240), details how the sensor in a moving device can be mounted on a MEMS-actuated pedestal, and moved in a cyclical fashion synchronized with the frame captures, to counteract motion blur. The multiple frames of imagery collected in such a capture arrangement can be combined to yield an enhanced resolution image (e.g., as is taught in Digimarc's published patent application 20080036886 and in U.S. Pat. Nos. 6,570,613 and 5,767,987).

Other 3D sensing arrangements are known, e.g., as identified in copending application Ser. No. 13/750,752, filed Jan. 25, 2013 (now published as 20130223673).

Above-noted patent application Ser. No. 13/842,282 details a particularly advantageous 3D camera sensor, employing photosites that are spectrally tuned—typically providing spectral responses at many more different wavelengths (e.g., at eight different wavelengths—some of which may be outside the visible range) than typical tri-stimulus (red/green/blue color-filter array) sensors of the previous art.

Another approach to 3D sensing is via an instrument that is touched to the skin, causing a membrane to deform in correspondence with the skin surface texture, forming what may be termed a skin print. Published patent application 20130033595 details such an arrangement, including a camera that captures imagery from the back side of the membrane, under oblique illumination that emphasizes the texture topography. See also Johnson, et al, Retrographic Sensing for the Measurement of Surface Texture and Shape, 2009 IEEE Conf. on Computer Vision and Pattern Recognition (attached to application 61/872,494). Such apparatus is now available from GelSight, Inc., of Cambridge, Mass., and may eventually be integrated into cell phones and other wearable computer systems.

Skin topology measured using such skin print techniques is believed to have a higher sensitivity and specificity for machine-based identification of certain skin conditions, as compared with 2D color imagery. Although "ground truth" skin topographies, which associate particular topographies with particular expert physician evaluations, are not yet available, these are expected to be forthcoming, when the utility of such measurements becomes widely known. Thus, another aspect of the present technology includes aggregating skin prints for a variety of medical conditions in a reference database—at least some of which also include expert diagnoses associated therewith. A related aspect involves deriving features from such reference prints, and then using such features in judging statistical similarities between a query skin print submitted by a user and the reference skin prints, to identify candidate diagnoses and other correlated information—as described earlier.

Skin surface minutiae can also be sensed otherwise, such as by systems for capturing human fingerprints. Examples are known from the published patent applications of Authen-Tec (subsequently acquired by Apple), including applications 20120085822 and 20110309482. Such sensors are already included in many laptop computers, and will doubtless soon appear in smartphones and the like.

Another image data collection technique comprises a flexible sheet with organic transistor circuits. The circuits can comprise photodetectors, as detailed, e.g., in Fuketa, et al, Large-Area and Flexible Sensors with Organic Transistors, 5th IEEE Int'l Workshop on Advances in Sensors and Interfaces, 2013, and Baeg et al, Organic Light Detectors—Photodiodes and Phototransistors Advanced Materials, Volume 25, Issue 31, Aug. 21, 2013, pp. 4267-4295, (both attached to application 61/872,494), and in references cited therein. Such media can also include integrated OLED photodetectors—providing controlled illumination.

As earlier noted, polarized light photography can also be useful with the present technology. This can be implemented with polarized illumination, or with one or more polarizers on the camera or image sensor. (See, e.g., Gruev, et al, CCD Polarization Imaging Sensor with Aluminum Nanowire Optical Filters, Optics Express 18.18 (2010): 19087-19094, which details a sensor having a polarizing filter associated with each pixel. The filters have four different orientations, offset by 45 degrees. By reading data from differently-filtered sets of pixels, different image polarizations are sensed.) By sensing imagery at different polarizations, different image features can be revealed and different image effects can be achieved (e.g., increased contrast). Some research also indicates that polarized light, when reflected, has two orthogonal components—one due to the skin surface morphology, and the other "back-scattered" from within the tissue.

While a user of the detailed system can submit a single image for analysis, it is sometimes preferable to submit several. As noted, these may comprise differently-focused, or differently-exposed images. They can also comprise lesion-centered images from different viewing distances, e.g., a close-up (e.g., where the lesion spans 25% or more of the image width), a mid-view (e.g., where the lesion spans between 5 and 25% of the image width), and a remote view (e.g., where the lesion spans less than 5% of the image width).

The remote view will typically show a sufficiently large body excerpt that the location of the lesion (e.g., arm, foot, hand, face) can be determined using known anatomical classification techniques. (Many smartphone operating systems, including those from Apple, include facial recognition capabilities—which begin by recognizing a face in an image.) Such lesion location data can then automatically be entered into the knowledge base, without requiring entry of such information by the user. (In other embodiments, software can present the user with a 3D avatar on which the user virtually draws, or taps, to indicate locations of skin lesions.) Seeing the lesion in the context of an identifiable body part also provides context from which the size of the lesion can be estimated. E.g., the average man's palm is 3.05 inches across, permitting the size of a lesion depicted in the same frame to be deduced.

As cameras and sensors continue to evolve, all three such views may be captured from a single camera position. For example, a telephoto lens may progressively zoom-out to capture the three just-referenced views. Or a high resolution sensor may have sufficient resolution that the former two views can be extracted from a remote view image frame. The software application may automatically obtain the three images—controlling the zoom or cropping a high resolution image as appropriate. (Desirably, each view is at least 1000 pixels in width.)

In some embodiments, the smartphone software offers guidance to the user in capturing the images, e.g., directing that the user move the camera away from the body until the software's body part classifier is able to identify the body part in the third view. Other direction, e.g., concerning lighting and focus, can also be provided.

It is also sometimes diagnostically useful to consider images from different parts of the body. If a lesion appears on a user's forearm, a second image may be submitted depicting the user's other forearm, or a skin patch that is not normally exposed to the sun—such as under the upper arm. Difference metrics can then be computed that compare the skin parameters around the lesion site with those from the other site. These data, too, can be submitted to the knowledge base, where similarities with other reference data may become evident.

Additional sensors will soon be commonplace on personal devices. Already appearing, for example, are smartphones equipped with multiple microphones. As further detailed below, in conjunction with a smartphone speaker, such a device is tantamount to an ultrasonic imager. Such a device can be pressed to the user's skin, and the skin them stimulated by ultrasonic sounds emitted by the speaker (or by other transducer—such as a piezo-electric actuator). The microphones—sensing reflection of such acoustic waves from inside the body, to the different microphone locations—provide information from which imagery can be constructed. Such ultrasonic imagery is more grist for the present mill.

Similarly, liquid lenses (e.g., marketed by Philips under the FluidFocus brand) may soon appear on smartphones, and enable new camera close-up and topological sensing capabilities.

In contact-based imaging (i.e., with the imaging apparatus touching the skin), the body location from which the image is captured can be electrically sensed using small amplitude electrical waveforms inserted in the body by a wearable computer device—such as the Google Glass device, or a wrist-worn device. Especially if different signals are introduced into the body at two locations, their distinctive superposition at the sensing site can accurately pinpoint the location of such site.

Ambient Light, Pose, Scale, etc.

Color is an important diagnostic feature in assessing dermatological conditions. However, skin color, as depicted in captured imagery, strongly depends on the "color" of the light that illuminates the skin. While dermatologists can control illumination conditions in their offices, most consumer image capture is performed under widely varying lighting conditions. To optimize performance of the detailed technologies, this variability should be mitigated.

Digital cameras commonly perform automatic white balance (AWB) adjustment. Various techniques are used. One technique examines the pixels in an image, and identifies one that is the brightest. This pixel is assumed to correspond to a white or shiny feature in the image, i.e., a feature that reflects all of the incident light, without absorbing any particular color. The component color values of this pixel are then adjusted to make it truly white (e.g., adjusting an RGB representation to {255,255,255}), and all other pixels in the image are remapped by similar proportions. Another technique averages all of the pixels in the image, and assumes the average should be a shade of grey (e.g., with equal red, green, and blue components—if represented in the RGB color space). A corresponding adjustment is made to all the image pixels, so that the average is remapped to a true shade of grey.

The former technique is ill-suited for skin photography because there is typically no white or specular pixel in the image. The latter technique is ill-suited because its premise—that the average pixel value is grey—is not true for skin images.

Professional portrait photographers sometimes position a calibration card at the edge of a family group, where it can be cropped-out before printing. The card includes various reference colors, including white and other known tones. Before printing, digital adjustments are made to the image to bring the depiction of colors on the calibration card to their original hues—thereby also color-compensating the portrait subject.

Thus one approach to the ambient light issue is for a user to capture imagery from a calibration card, and send this image to the central system, accompanying the skin image(s). The system can then color-compensate the skin image(s), based on the depiction of colors in the calibration card image.

However, such calibration cards are not readily available, and cannot typically be electronically distributed to users for printing, due to color variability among consumer printers.

Applicant has found that various other materials can suffice in lieu of calibration cards.

One is a white envelope. The "white" on color calibration cards is a colorimetrically true white, whereas there is a great deal of variability in what passes for white among the lay public. But applicant has found that white postal mail envelopes tend to be consistent in their color—especially at the red end of the spectrum that is important for skin photography (there is more item-to-item variability at the violet end of the range). While not "true white" in a colorimetric sense, such envelopes are generally consistent enough to serve as a color reference.

So one approach to ambient light issues in consumer skin photography is to direct the user to capture imagery from a white envelope, under the same lighting conditions as the skin photograph(s). This image can be sent to the central system, where the skin photograph can be color-corrected based on the envelope photograph.

The entire envelope needn't be photographed—just a fraction will do. In one method, a part of the envelope substrate is torn or cut off, and placed on the skin, within the camera's field of view. But such arrangement a single image capture can suffice. Meanwhile, at the central system, the illumination-corrected, reflected color spectra from an assortment of white postal envelopes are captured and averaged, and used as reference data against which images received from end users are color-corrected.

(It will be recognized that placing a piece of a white envelope in the field of view of a skin photograph can allow automatic white balance correction of the image by the camera—if the camera is using the former of the above-described two AWB techniques. However, the details of a particular camera's AWB algorithm are not generally known. The central service may, however, investigate the AWB techniques used by popular smartphone cameras. By examining the metadata that commonly is packaged with smartphone imagery, e.g., in the form of EXIF header data in an image file, the central system can determine the type of camera with which a user image was captured. If the image was captured from one of the cameras using the former AWB technique, and automated image analysis finds that the image includes an area of white next to skin tone, the system can infer that appropriate color correction has already been applied by the camera.)

Another commonly available color reference—for those so-inclined—is oxygenated blood. Blood exhibits a consistent color spectrum despite race and other variable factors. If a drop of blood is thick enough to mask the underlying skin pigment, its color can be sensed and again used to reveal color information about the illumination.

Color calibration can also be performed with banknotes. Banknotes are typically printed with extremely high tolerances, and consistent ink colors. Desirably, a banknote excerpt having colors near the skin tone range is employed. While US currency is commonly regarded as green, in fact the US $20 bill has areas of skin-like tones to the left and right of the Jackson portrait. (The US $10 has areas of reddish tones.)

In accordance with this method, the user captures images of the skin, and of a US $20 banknote, under the same illumination conditions. Both the skin image and the banknote image are then sent to the central system. The central system again compares the spectrum found in the received banknote image with reference data, and determines a spectral correction function detailing variance between the received banknote image and reference data. The system then applies this correction function to the received skin image, to effect color correction.

Since color correction is primarily needed for skin tones, areas of a banknote lacking such colors can be omitted in performing the spectrum measurement and correction. The central system can virtually identify the relevant areas of the banknote artwork by reference to image features—such as SURF or SIFT keypoints, or by other pattern-matching techniques. An area bounded by such points can be virtually "clipped" from the artwork, and used as the basis for comparison against a similarly-clipped set of reference data. FIGS. 3A and 3B show the banknote artwork, and a representative clipped region spanning most of the skin tone region. This area is defined by "corner" features in the original artwork (e.g., the upper right corner of the letter E in " . . . PUBLIC AND PRIVATE;" the lower left corner of the A in AMERICA; etc.), and omits artwork that can vary between banknotes, i.e., the serial number.

The reference data is acquired by a reflectance spectroscopy technique that involves masking the banknote with a flat black mask—revealing only the clipped region—and illuminating with a light source whose spectrum is measured or otherwise known. Reflected light is sensed by a spectrometer, yielding a set of data indicating intensity as a function of wavelength. This measured data is then adjusted to compensate for the known spectrum of the light source.

FIG. 4 shows such a reference spectrum measured for both the Jackson portrait excerpt shown in FIG. 3B (the lower line), and for a sample white postal envelope.

The contemplated system may serve users in diverse countries. Desirably, suitable calibration objects are identified so that one or more is available in each of these countries. The central system can examine the incoming imagery, and compare against a catalog of calibration objects to recognize which object is being used. Thus, a customer may choose to use a Mexican 100 peso note as a reference, and the central system will recognize same and apply the corresponding correction function.

It will be recognized that the above-described procedures for effecting correction of colors due to ambient lighting variability also effect correction of colors due to camera sensor variability. That is, if one camera tends to emphasize greens, and another camera tends to emphasize reds, the imagery from both will be normalized to a consistent standard using the arrangements detailed above.

The procedure employing a printed object in the image frame with the skin (as opposed to a white object) also allows the system to assess the brightness of the imaged scene. Cameras have limited dynamic range. If a scene is too brightly lit, the camera's component red, blue and green sensors can no longer sense variability between different parts of the image. Instead, each outputs its full maximum signal (e.g., 255, in an 8-bit sensor). Faithful color sensing is lost. Similarly with too little illumination; differently-colored areas are again indistinguishable. By imaging a known printed object, such as a banknote, such over- and under-exposure can be sensed (by comparison of detail in the sensed imagery with detail in reference imagery), and the user can be prompted to change the illumination and submit a new image, if needed.

If a known printed object is used as a color reference object, the object artwork also enables other information to be sleuthed, such as scale, provided the object is depicted in the same image frame as the skin condition. To illustrate, the distance between the centers of Jackson's eyes on the US $20 banknote is 9 mm. If such a banknote is photographed next to a lesion, and the distance between Jackson's eyes spans 225 pixels, and the lesion spans 400 pixels, then the lesion is known to have a width of 16 mm. Dimensions of other features in the image can be similarly determined.

If the printed object lies in the same plane as the skin, then the pose of the camera relative to the skin can also be determined—based on apparent geometrical distortion of the object. That is, if the camera axis is not perpendicular to the skin, then perspective distortion will cause features depicted in some parts of the frame to be larger, or smaller, than would be the case with a perpendicular pose. By reference to the known aspect ratio of features on the printed object, and comparison with their aspect ratio in the captured imagery, the angle from which the image was captured can be sleuthed, and a corrective counter-distortion can be applied. (The camera's optic function can also be considered in the analysis, to account for the expected apparent distortion of features displaced from the center of the image frame. For example, the circular seal of the US Federal Reserve System, on the left side of a banknote, may be subtly distorted from round—even with a perpendicular camera pose—if the seal is not at the center of the image. Such distortion is expected, and the analysis takes such normal artifacts of perpendicular poses into account.)

In the case of banknotes, still finer pose determinations can be made, based on security features that have different appearances with different viewing angles. Color-shifting inks, security threads with microscopic lenses, and kinegrams, are of this sort. The central system can collect reference information quantifying the appearance of these features at different viewing angles. When a user-submitted image is recognized to have such a banknote security feature depicted, its rendering in the image can be matched with the reference information to determine the angle at which it is being viewed—from which the viewing angle of the skin lesion can then be determined. (In many such measurements, the color of the security feature shifts with viewing angle. Thus, it is desirable to first perform color-correction on the user-submitted imagery, before analyzing pose in this fashion.)

Another calibration token that can be placed on the skin for image capture is a coin. Again, a variety of different coins may be recognized by the central system—and from their known attributes, scale and pose determinations can be made—just as with the banknote arrangement described above. Also, many coins exhibit the specular reflection used by many cameras for automatic white balance.

Other commonly available items that can be placed in the image frame to serve as props for color correction and/or scale measurement include the white cord of Apple USB cables and earbuds, and the USB plug itself. The user's thumb (or other finger) can also be put into the image frame—providing a scale reference and also skin tone information.

Another approach to dealing with ambient light variability is to employ the smartphone's front-facing camera.

Smartphones are commonly equipped with two cameras—one on the front, facing the user, and one on the rear. The latter is typically used for capturing skin imagery. But the former can be used to capture image data from which ambient lighting can be assessed. The field of view of the front-facing camera can include a variety of subjects—making its automatic white balance determination more trustworthy than the rear-facing camera (whose field of view may be filled with skin).

In accordance with this aspect of the technology, an automatic white balance assessment is made using the front-facing camera, and resulting information is then used in AWB-processing of skin imagery captured by the rear-facing camera.

Still another approach to dealing with ambient light variability is to use flash illumination. The light emitting diodes (LEDs) used for camera flashes have relatively consistent spectra among instances of a particular model (e.g., iPhone 5 cameras). Reference data about flash spectra for popular camera models can be compiled at the central system. Users are then instructed to capture the skin image in low ambient light conditions, with the camera flash activated. When the central system receives such imagery, it examines the header data to determine the camera model involved, and flash usage. The system then applies a color correction that corresponds to the flash spectrum for that model of camera.

Low ambient light can sometimes be difficult to achieve. And adapting technical methods to the user, rather than adapting user actions to the technology, is generally preferable. In accordance with another aspect of the technology, flash is used in conjunction with ambient lighting for color correction.

In one such method, two images are taken in quick succession—one including an LED flash, and one not. (Video mode can be used, but resolution is typically better in a still image capture mode.) Both images include the ambient light, but only one includes the flash. Subtracting the two images leaves a difference image that is illuminated by the LED flash alone—mitigating the uncertainty due to unknown ambient lighting. (The images can be spatially registered prior to subtraction, using known registration techniques, to account for slight motion between frames.) Again, the resulting image can be adjusted to compensate for the spectrum of the LED flash. Software on the user device can effect such image capture, flash control, and differencing operation.

Still another technique for color compensation is by reference to measured norms of skin coloration. While skin comes in a variety of colors, these colors comprise a tiny fraction of the universe of possible colors. This is particularly true when skin color is represented in the CIELAB color space. This range is narrowed still further if the user's race is known, e.g., entered via the user interface of a smartphone app, or recalled from stored user profile data.

(In smartphones equipped with front- and rear-facing cameras, the former can be used to capture a picture of the user—since the user typically operates the phone facing towards the screen. Known techniques can assess the user's race (and gender) from facial imagery—avoiding the need for the user to enter this information. See, e.g., Lyons, et al, Automatic Classification of Single Facial Images, IEEE Trans. on Pattern Analysis and Machine Intelligence, Vol. 21, No. 12, 1999, pp. 1357-1362 (attached to application 61/872,494), and references cited therein. The race assessment can be performed by smartphone app software, so that the user's facial image is not sent from the phone.)

Since the user will typically frame a captured image so that a skin condition of concern is at the center, a better indication of the user's normal skin color may be obtained by sampling away from the center, e.g., at the edges. An average color, based on samples taken from a variety of peripheral image locations, can be computed. (Samples should be checked to assure that a location does not correspond to clothing or other non-skin feature. Color consistency and/or segmentation techniques can be used.) This baseline skin color can then be checked against statistical color norms—for the user's race, if known. If this baseline color is outside of the statistical norm (e.g., within which 99%, or 99.9% of the population falls), then an adjustment is made to the captured imagery to shift the image colors so that the average falls within the norm. (The shift can move the average skin tone to the nearest edge of the norm region—as defined in the CIELAB color space—or to the center of the norm region.)

For more on norms of skin colors, and related information, see, e.g., Zeng, et al, Colour and Tolerance of Preferred Skin Colours, Color and Imaging Conference, Society for Imaging Science and Technology, 2010 (attached to application 61/872,494), and references cited therein.

While reference was made to assessing the size of skin features by reference to another article (e.g., a coin) in the image frame, other techniques can also be used.

One is by photogrammetry, using camera and image data. For example, if the image metadata indicates the camera autofocus (subject distance) was set at 6 inches, and the camera is known to capture a field of view that is four inches wide in that focal plane, then an image feature that spans a tenth of the width of the frame has a width of 0.4 inches. (Instead of autofocus information, data from a smartphone's proximity detector can alternatively be used. Such detectors primarily rely on capacitive techniques and are presently of short range, e.g., 2 cm., but longer range sensors are under development.)

An allied technique, also from the field of photogrammetry, is bundle adjustment. (See, for example, Triggs et al, Bundle Adjustment—A Modern Synthesis, Proceedings of the International Workshop on Vision Algorithms. Springer-Verlag., pp. 298-372, 1999). In bundle adjustment algorithms, multiple images taken from different locations and/or directions are exploited to jointly produce estimates of the optical view parameters of the camera(s) and a 2D or 3D model of the scenes imaged. While bundle adjustment originated in the photogrammetry community, it has found much recent use in the computer science field, where is a fundamental component of shape from motion algorithms. Partial knowledge of the characteristics of the camera(s) can be used to improve the accuracy of the scene model. In the case of skin images captured with a smartphone, the multiple images may be made by passing the camera over the patch of skin. By exploiting the redundancy provided by images taken from different perspectives, it is possible to provide scale to the images. Since smartphones typically also have IMUs and/or gyroscopes, it is possible to improve upon the performance of these algorithms by feeding in this sensor information as side information.

Another scaling technique relies on known biometric norms. For example, in adults, the inter pupillary distance (the distance from the center of one eye pupil to the center of the other) is about 62 mm. A variety of other consistent biometric measurements are known (going back to the carpenter's "Rule of Thumb" of antiquity), or can be gathered from analysis of data. Some are absolute measures (e.g., the inter pupillary distance is about 62 mm), and others are ratios (e.g., the ratio of forearm length, to forearm plus hand length, is about 0.58). Some such measures are tightly clustered, based on the user's gender and height. Image classification techniques can be applied to user imagery to recognize pupils, a thumb, a fingernail, a forearm, a hand, etc. From known biometric measures, the size of a skin lesion can be inferred.

Other scaling techniques rely on such biometric norms, in conjunction with imagery from front- and rear-facing cameras. Consider a user taking a picture of a lesion on their forearm. The forearm can be recognized from imagery captured by the smartphone camera. The smartphone is positioned somewhere between the user's face and forearm, but its distance from the arm is unknown (disregarding auto-focus and other estimation techniques). However, previous experimentation shows that a typical user tends to hold their smartphone camera about 12 inches from their face, when viewing their forearm.

The front-facing camera can capture an image of the user's face. While the distance from the phone to the forearm is unknown, the distance from the phone to the face can be deduced from the pixel sizing of the inter pupillary distance. (The closer the phone is to the face, the larger the distance between the user's pupils becomes—in terms of pixel spacing.) Based on previous experimentation, or based on analysis of the camera's optics, the pixel spacing between the depicted pupils directly correlates to the distance between the front-facing camera and the user's face. Subtracting this value from 12 inches yields the viewing distance between the smartphone and the user's forearm. From this viewing distance, and information about the camera's optics, the size of features on the skin can be deduced.

Similarly, the color of facial skin depicted in imagery captured by the front-facing camera, can be used in assessing the color of skin depicted in imagery captured by the rear-facing camera. In one scenario, the facial skin may be used as a reference skin color. (Facial recognition techniques can be applied to identify the eyes and nose, and from such information the portion of the imagery depicting cheeks and forehead can be determined. Skin facial color can be sampled from these locations.)

Relatedly, eye color is a useful tool in establishing an expected skin color. For example, a grey iris is most commonly associated with people of Northern and Eastern European descent, for whom norms of skin coloration can be established. Ethnic associations with other eye colors are also well known. (See, e.g., the Wikipedia article "Eye color.")

If imagery of the subject skin condition—captured by the rear-facing camera—exhibits a skin color that is different than this reference color, such difference may be taken as a diagnostic indicia. Likewise the reference facial skin color can be used in segmenting features from the skin imagery captured by the rear-facing camera.

In some instances, the skin imaged by the rear-facing camera (e.g., on the user's forearm) may be illuminated differently than the facial skin imaged by the front-facing camera. For example, the user may have oriented a fluorescent desk lamp towards their arm to provide more light. As noted, such lighting changes the apparent color of the skin. Relatedly, the skin imaged by the rear-facing camera may be within a shadow cast by the phone. By comparing the skin colors imaged by the front- and rear-facing cameras, such illumination issues can be detected (e.g., by difference in chrominance or luminance), and corrective compensations then applied.

Longitudinal Studies

As noted, the evolution of a skin condition over time can be useful in its assessment. Images of a skin condition taken at different times can be shown in different manners to illustrate evolution of the condition.

Desirably, the images are scaled and spatially aligned (i.e., registered), so that a consistently-sized and oriented frame of reference characterizes all of the images. This allows growth or other change of a lesion to be evident in the context of a generally unchanging background.

Images can be scaled and aligned using known techniques. Exemplary is by reference to SIFT or SURF features, in which robust feature key points that are common throughout images are identified, and the images are then warped (e.g., by an affine transform) and rotated so that these points become located at the same positions in each of the image frames. (One such arrangement is detailed in applicant's patent application 20120208592.)

To facilitate this operation, it is desirable (although not essential) to first identify the extent of the lesion in each of the frames. Known boundary-finding algorithms can be applied to this task (sometimes predicated on the assumption that the lesion of interest is found in the center of the image frame). Once the boundary of the lesion in each image is identified, the lesion can be masked (or flooded with a uniform color) so that the key point identification method does not identify key points from the lesion or its boundary. This reduces the key point count, and simplifies the later matching of common keypoints between the images.

Body hair can also be a source of many superfluous key points in the different image frames—key points that typically don't help, and may confound, the image registration process. Thus, the images are desirably processed to remove hair before key points are determined. (There are a variety of image processing algorithms that can be applied for this task. See, e.g., Abbas, et al, Hair Removal Methods: a Comparative Study for Dermoscopy Images, Biomedical Signal Processing and Control 6.4, 2011, pp. 395-404 (attached to application 61/872,494), and references cited therein.)

Key points are then extracted from the imagery. Depending on the magnification of the images, these points may be associated with nevi, hair follicles, wrinkles, pores, pigmentation, textures, etc. If the imaging spectrum extends beyond the visible, then features from below the outermost layer of skin may be evident, and may also serve as key points.

A key point matching search is next conducted to identify corresponding key points in the images.

One image is next selected as a reference. This may be, e.g., the most recent image. Using the extracted key point data, the rotation and warping required to transform each of the other images to properly register with the reference image is determined. These images are then transformed in accordance with such parameters so that their key points spatially align with corresponding key points in the reference image. A set of transformed images results, i.e., the original reference image, and the rotated/warped counterparts to the other images.

(If the lesion were on a flat, rigid surface, then each skin image would be related to the others by a simple rotation and affine transform. This is generally a useful approximation for all cases. However, due to the curvature of some skin surfaces, and the fact that skin may stretch, a more generalized transform may be employed to allow for such variations.)

One form by which the transformed images can be presented is as a stop-action movie. The images are ordered by date, and rendered sequentially. Date metadata for each image may be visibly rendered in a corner of the image, so that the date progression is evident. The sequence may progress automatically, under software control, or each image may be presented until user input (e.g., a tap on the screen) triggers the presentation to advance to the next image.

In some automated renderings, the software displays an image for an interval of time proportionate to the date-span until the next image. For example, if images #1-4 were captured on successive Mondays, and then two Mondays were missed before images #5-8 were captured (again on successive Mondays), then images #1-3 may be presented for one second each, and image #4 may be presented for three seconds, followed by images #5-7 presented for one second each. (Image #8—the last image—may remain on the screen until the user takes a further action.) A user interface control can be operated by the user to set the speed of rendering (e.g., the shortest interval that any image is displayed—such as one second in the foregoing example, or the total time interval over which the rendering should occur, etc.).

A different form by which the transformed image set may be viewed is as a transitioned presentation. In this arrangement, a video effects transition is employed to show information from two or more image frames simultaneously on the display screen. In a simple arrangement, image #1 (the oldest image) is displayed. After an interval, image #2 begins to appear—first as a faint ghosting effect (i.e., a low contrast overlay on image #1), and gradually becoming more definite (i.e., increasing contrast) until it is presented at full contrast. After a further interval, image #3 starts to appear in like fashion. Optionally, the older images can fade out of view (e.g., by diminishing contrast) as newer images ghost-into view. At different times there may be data from one, two, or more images displayed simultaneously. As before, the progression can be under software, or user, control.

In the above examples, the renderings may employ the images from which hair was digitally removed (from which key points were extracted). Alternatively, the renderings may employ the images with hair undisturbed.

In some arrangements, the rendering sequences can be accompanied by measurement data. For example, a textual or graphical overlay added to a corner of the presentation may indicate the width or area of the depicted lesion, e.g., an area of 12 mm$^2$ in the first image, 15 mm$^2$ in the second image, 21 mm$^2$ in the third image, etc. Similarly, for each frame, the color or darkness of the lesion, or its boundary irregularity or its texture, may be quantified and expressed to the user.

In still other arrangements, such information is not presented with each image in the series. Rather, at the end of the rendering, information is presented detailing a change in the lesion from the first frame to the last (e.g., the lesion has increased in area by 83% in 7 weeks).

Such statistics about the lesion, and its changes, can also be presented as a textual or graphical (e.g., with Cartesian graphs) report, e.g., for emailing to the user's physician.

It will be recognized that the skin features from which the key points are extracted define a characteristic constellation of features, which permits this region of skin to be distinguished from others—a fingerprint of the skin region, so to speak—and by extension, a fingerprint of the user. Thus, even if a skin image is submitted to the central server data identifying the user, this characteristic fingerprint information allows the system to associate the image with the correct user. This may be used as a privacy-preserving feature, once a characteristic constellation of skin features has been initially associated with a user. (This distinctive constellation of features can also serve as a biometric by which a person can be identified—less subject to spoofing than traditional biometrics, such as friction ridges on fingertips and iris pattern.)

It will further be recognized that features surrounding an area of interest on the skin effectively serve as a network of anchor points by which other imagery can be scaled and oriented, and overlaid, in real time. This permits an augmented reality-type functionality, in which a user views their skin with a smartphone, and a previous image of the skin is overlaid in registered alignment (e.g., ghosted), as an augmentation. (A user interface control allows the user to select a desired previous image from a collection of such images, which may be stored on the user device or elsewhere.) As the user moves the phone towards or away from the skin—changing the size of the lesion depicted on the camera screen, the size of the overlaid augmentation similarly changes.

As the size of the knowledge base increases, so does its utility. At a sufficiently large scale, the knowledge base should enable detection of pathologies before they become evident or symptomatic. For example, a subtle change in skin condition may portend a mole's shift to melanoma. Development of a non-uniformity in the network of dermal capillaries may be a precursor to a cancerous growth. Signals revealed in skin imagery, which are too small to attract human attention, may be recognized—using machine analysis techniques—to be warning signals for soon-to-be emergent conditions. As imaging techniques advance, they provide more—and more useful—weak signals. As the knowledge base grows in size, the meanings of these weak signals become clearer.

To leverage the longitudinal information in the knowledge base, image information depicting a particular user's condition over time must be identifiable from the data structure. As described above, the unique constellation of features associated with a particular region of skin on a user, allows all images depicting this patch of skin on this user to be associated together—even if not expressly so-identified when originally submitted. The FIG. 2 data structure can be augmented by a further column (field) containing a unique identifier (UID) for each such patch of skin. All records in the data structure containing information about that patch are annotated by the same UID in this further column. (The UID may be arbitrary, or it may be derived based on one or more elements of user-related information, such as a hash of one of the user's image file names, or based on the unique constellation of skin feature points.)

As data processing resources permit, the central system can analyze the longitudinal information to discern features (e.g., image derivatives) that correlate with later emergence of different conditions. For example, if the system finds a hundred users diagnosed with melanoma for whom—in earlier imagery—a network of capillaries developed under a mole that later become cancerous, and this network of capillaries is denser, by a factor of two- to three-times, than the density of capillaries in surrounding skin, then such correlation can be a meaningful signal. If a new user's imagery shows a similar density of capillaries developing under a mole, that user can be alerted to historical correlation of such capillary development with later emergence of melanoma. Such early warning can be key to successful treatment.

In the example just-given, the correlation is between a single signal (dense capillary development) and a cancerous consequence. Also important are combinations of signals (e.g., dense capillary development, coupled with die-off of hair in the mole region). Known data mining techniques (including supervised machine learning methods) can analyze the knowledge base information to discover such foretelling signals.

Naturally, information discovered through such analysis of knowledge base information is, itself, added to the knowledge base for future use. As new correlations are discovered, new insight into previously-submitted imagery may arise. The central system can issue email or other alerts to previous users, advising them of information that subsequent data and/or analysis has revealed.

While the foregoing discussion concerned studies of a single skin site, it was earlier noted that information about skin conditions at other places on the body may also be relevant. Thus, in conducting such longitudinal studies, consideration may also be given to information in the knowledge base, and in the user data, concerning other skin sites. (Such other skin site information may be considered as another element of user metadata, noted earlier, all of which should be employed in discovering patterns of correlation.)

Application of machine learning technologies for cancer prediction is a growing field of endeavor. See, e.g., Cruz, et al, Applications of Machine Learning in Cancer Prediction and Prognosis, Cancer Infom., No. 2, 2006, pp. 59-77; Bellazzi, et al, Predictive Data Mining in Clinical Medicine—Current Issues and Guidelines, Int'l J. of Medical Informatics, V. 77, 2008, pp. 81-97; and Vellido, et al, Neural Networks and Other Machine Learning Methods in Cancer Research, in Computational and Ambient Intelligence, Springer, 2007, pp. 964-971 (attached to application 61/872,494), and references cited therein.

Image Registration Using Multi-Spectral and Hyper-Spectral Imagery

The previous discussion, outlining approaches for registering images in longitudinal studies, can benefit further when those images might contain more than just the standard RGB layers of a color image. The reason for this is that skin texture, hair, lesion boundaries—and a much longer list of skin attributes than just these—all can be enhanced in their discrimination and contrast by their representations as higher dimensional data structures. Many of the practical challenges encountered in trying to perform these registration techniques on standard color imagery—such as feature point fading between one day where a patch of skin is drier and giving rise to distinct line features and the next day where a person has applied skin moisturizers and has effectively removed those lines—can be overcome through the seeking and measurement of higher dimensional image features. The detailed warping arrangements whereby stretched skin in one image must be re-stretched to match another image also can make use of such higher dimensional hyper-spectral features.

Image Registration Through Motion

Another way to enhance skin-patch and/or lesion registration is through teaching users of such an app to use and perfect the motion of their camera itself while gathering imagery of their skin. The resultant motion of the skin regions manifested in the imagery itself, often combined with the on-camera motion information data common to almost all smartphones, allows for further degrees of information to be utilized in precise millimeter and sub-millimeter scale matching of some given skin sample and the imagery of the same skin taken weeks, months or even years earlier. Many detailed features change often drastically over such lengthy time periods, where the use of motion imagery and the resultant parallax data information can help to derive additional shape and perspective information, all of which assists in the generic task of stabilizing the viewing and interpretability of often quite dynamic skin conditions and lesions.

Finger-Slide Viewing of Time Sequences

As is familiar in certain smartphone user interfaces, another method of viewing skin conditions over time is to finger slide back and forth in time through the registered imagery. This doesn't need to be limited to the viewing of pathological conditions either; it can be as simple as the desire of a teenager to simply view how their make-up appearance has changed over the last few weeks, or a review of what color of eye-liner they might have utilized two weeks earlier. In such non-ailment applications of this technology, further user interface choices can be presented to a user once they have honed in on some particular earlier imagery, such as displays of the very particular brands and types of commercial products may have an association with a particular earlier date. Likewise, back in a pathological context, a user may be trying various treatments for acne for example, and they will want to be able to finger scroll between images taken when they were trying brand X, and images when they we trying brand Y.

Managing Cultural Tensions Inherent in Automated Screening and Computer Assisted Diagnosis (CAD)

Those familiar with the early 21st century growth in the use of computers in helping to detect and diagnose disease are equally familiar with the large divisions in the cultural acceptance of this inevitable trend. It is difficult to disagree with the statement, "both sides are right." If we caricaturize one camp as the proponents who correctly claim that computers can expand health care well beyond the wealthier classes and countries, and the other camp as not necessarily opponents but critics who correctly claim that poorly executed health services often violate the Hippocratic oath, then we find ourselves in a stalemate that only time and the market will slowly break up.

This disclosure presents humble yet explicit technological components meant to directly address these tensions as opposed to trying to ignore them and wait for them to simply go away. That will take a while. Specifically, the numerous crowd sourcing aspects previously disclosed should all be implemented with clear delineations between information derived from clinically licensed sources versus everything else. Color schemes, specially designed logos and text treatments . . . such technically implemented graphic clues should all be used as templates to demarcate "results" information sent back to users of these systems. As an example, if automated processes produce probability results which tend to indicate concern over some skin patch or patches, any positivistic results sent back to a user should be packaged in uniformly recognizable graphic forms which are associated with the classic response of " . . . comparisons of your results with thousands of others tend to suggest that you seek licensed medical examination . . . " On the other extreme, if results tend strongly toward a "normal" or benign classification for all submitted imagery, the graphic formatting and language can indicate the null result, yet still reinforce the notion that users should nonetheless use their instincts in seeking licensed medical assistance despite the null results of some particular session.

These ideas can readily be implemented by considering them as a discrete filter stage sitting between the software/analysis engines that are tasked with producing probabilistic results on submitted imagery, and the GUI stages of user interaction. This filtering is not at all a GUI matter; it is fundamentally about ensuring that centuries' old common medical practices are followed in the communication with a user. This discrete filtering will by no means solve the deep cultural tensions inherent in these activities, but they can form a highly explicit balance between the truths of both camps described above. The broadest goal is to reach out to a broader set of actual at-risk individuals, providing guidance toward the seeking of licensed medical treatment. Likewise, for those individuals who in actuality are not at risk for the conditions they are worried about, it is still no place for an automated service to do anything more than simply indicate null results. No trace of "assurances" can be part of a response unless a licensed practitioner is actively involved in a session, with full disclosure of that involvement and reference to the professional acceptance of that involvement. All in all, then, this discrete filter might be named the "best medical practices" filter, and all communications concerning test results should be mandated to pass through this discrete filter.

The classic term "screening" has been used for decades now, largely dealing with these broader concepts. Though the lay-public often confuses screening with diagnosis, the medical profession has put forth enormous efforts to educate the public about their differences. Furthermore, many medical professionals will consider any automated service which does not have a case-by-case medical practitioner involved to not even be worthy of the term "screening." This is a legitimate viewpoint, especially as the law allows for any solution vendor or medicinal product manufacturer to make generic claims toward medical efficacy. But here again the term "screening" can become a technically implemented element of the crowd-sourced elements described in this disclosure by simply presenting results in the fully disclosed context in which those results were derived. Specifically, deliberately borrowing from known cultural norms, results can be phrased as "over 1000 other individuals have submitted images very similar to yours, and according to an ad hoc survey of those individuals, 73% sought medical advice . . . " The variations and permutations on these themes are vast.

Again, technically, this kind of data and the generation of such statements require actual crowd-source data gathering and storage, then linked into a results filter as described above. The actual process of this particular type of screening is fully disclosed both in its methodologies as well as in the phrasing of results. It thus earns the term screening because that's exactly what it becomes, a crowd-sourced screening phenomena. Its eventual efficacy will be determined by the quality of its ultimate results and growth in its user base.

Quick and Economic Whole-Body Skin Screening—Early Melanoma Screening Room

Fresh off the topic of screening, this disclosure next details how the current art of whole-body dermatological photography can transition toward a fully licensed dermatological screening test, emulating the cultural norms of pap smears and colonoscopies.

The current art in whole-body scanning is illustrated by Canfield Imaging Systems, which operates imaging centers in cities throughout the U.S. At these facilities, patients can obtain whole-body imagery, which is then passed to their physicians for review. Aspects of the Canfield technology are detailed, e.g., in U.S. Pat. Nos. 8,498,460, 8,218,862, 7,603,031, and 20090137908.

A basic aspect of an illustrative early melanoma screening room (EMSR) is simple: build a transparent phone booth (or cylinder) surrounded with cameras and synchronized lighting. For example, the booth may comprise lighting with, e.g. 16 to 32 LED spectral bands (some into the near-IR), and a dozen or two dozen RGB and/or black and white cameras. (See, e.g., patent application documents 20130308045, and Ser. No. 14/201,852.) Shaving, or an alcohol or other skin treatment, may be employed in certain cases. People get naked or put on a bathing suit, get inside, and raise their arms—as in the TSA imaging booth. Five or fifteen seconds later they are done. They can wear small goggles if they like, but closing eyes, or even having them open, will probably be fine (and will probably have to be, for FDA approval). Maybe two or three poses for normal extra data gathering, dealing with odd reflections and glare, different skin-surface normals, so all in all a non-surgical, less-than-one-minute affair.

The computer churns for another 30 seconds conducting image analysis and comparison with reference data, and either gives a green light, or, perhaps in a non-alarming way and still "routine," a low threshold is set such that a patient is asked to go into a second room where a technician can focus in on "concern areas" using existing state-of-the-art data gathering methods on exact areas, including simple scrape biopsies. (The technician views results from the scan, with "guidance" from the software, in order to flag the patient, point out the areas of concern, and instigate the second-room screening.) Practicing clinicians also can be more or less involved in the steps.

This is pap-smear, colonoscopy, cultural 101 kind of thinking . . . do it first when you are 25, then every 5 years, or whatever. Get it close to the pap-smear kind of test cost wise, the rooms themselves shouldn't run over $5 to $10K full manufacturing cost; no need to get too crazy on the hardware technology.

The market demand, of course, is to discriminate normal skin from melanoma and other pathologies. The explicit target would be detecting earlier and earlier stage melanoma, seeing how early one can get. Receiver operating characteristic (ROC) curve studies are the industry norm next step, seeing how quickly true positive detections can occur before annoying levels of false positives start to kick in. Since this is meant to be a very early screening method, this favors tilting the ROC curves toward "detect more," so that again, a technician can do "no big deal" secondary screening using existing methods and weed out the slightly larger level of false negatives due to higher ROC thresholds. So this is also a cost-based measure, providing better guidance toward "who" should be getting referred to more expensive existing screening methods.

The real point of EMSR is early detection. Increased quantity of care at current quality levels and current cost levels is also the point, with averted mortality also being a direct cost benefit beyond saving a person's life. Even six months, but better yet 1 to 2 years of advanced detection will produce stunning and clear increases in survival rates.

FIG. 5A shows a schematic sectional view looking down into a cylindrical booth (e.g., seven feet in height, and three feet in diameter, with an access door, not particularly shown). Arrayed around the booth (inside, outside, or integrated into the sidewall) are a plurality of light sources 52 and cameras 54.

The depicted horizontal ring array of light sources and cameras can repeat at vertical increments along the height of the booth, such as every 6 or 18 inches (or less than 6, or more than 18). The lights and cameras can align with each other vertically (i.e., a vertical line through one light source passes through a series of other light sources in successive horizontal rows), or they may be staggered. Such a staggered arrangement is shown in FIG. 6A, in which successive rows of lights/cameras are offset by about 11 degrees from each other.

FIG. 6B shows another staggered arrangement, depicting an excerpt of the side wall, "unwrapped." Here, successive horizontal rows of light sources 52 (and cameras 54) are offset relative to each other. Moreover, in this arrangement, the light sources 52 are not centered between horizontally-neighboring cameras, but are offset.

Although not depicted, the light sources needn't be interspersed with cameras, with the same number of each. Instead, there may be a greater or lesser number of light sources than cameras.

Similarly, the light sources needn't be arrayed in the same horizontal alignment as cameras; they can be at different vertical elevations.

Light sources and cameras may also be positioned below the person, e.g., under a transparent floor.

Desirably, the light sources are of the sort detailed in applications 20130308045 and Ser. No. 14/201,852. They may be operated at a sufficiently high rate (e.g., 40-280 Hz) that the illumination appears white to human vision. The cameras transmit their captured imagery to a computer that processes the images according to methods in the just-noted patent documents, to determine spectricity measurements (e.g., for each pixel or other region of the imagery). Desirably, errors in these measurements are mitigated by the techniques detailed in these documents. The imagery is then divided into patches (e.g., 1, 2, or 5 cm on a side) and compared against reference imagery, or applied to another form of classifier. All of the imagery can be processed in this fashion, or a human or expert system can identify patches of potential interest for analysis.

In other embodiments, the patient can stand on a turntable that rotates in front of a lesser number of cameras and light sources, while frames of imagery are successively captured. Thus, a full "booth" is not required. Such arrangement also captures imagery at a range of different camera-viewing and light-illuminating angles—revealing features that may not be evident in a static-pose capture of imagery. (A turntable also allows hyperspectral line sensors to be employed in the cameras, with 2D imagery produced from successive lines as the turntable turns. Such line sensors are available from IMEC International of Belgium, and capture 100 spectral bands in the 600-1000 nm range. Of course, 2D sensors can be used as well—including hyperspectral sensors. One vendor of hyperspectral 2D sensors, sometimes termed imaging spectrographs, is Spectral Imaging Ltd. of Finland.)

In some embodiments, 3D reconstruction techniques (e.g., SLAM) are applied to the captured imagery to build a digital body map. In such a map/model, not only the size, but images, of every suspicious location are recorded over time. In some implementations, images of the entire body surface can be recorded, allowing an examining physician to virtually fly, Google-Earth-like, over the patient's modeled body surface, pausing at points of interest. If historical images are available, the physician can examine the time-lapse view of changes at each location, as desired. Some useful subset of the spectral bands can be used to do the mapping. If desired, the patient's body map can be morphed (stretched and tucked and squeezed, etc.) to a standardized 3D body shape/pose (of which there may be a dozen or more) to aid in automated processing and cataloging of the noted features.

User Interface and Other Features

In reporting results from crowd-sourced data repositories back to users, care should be taken not to offend. In one aspect, the user software includes options that can be user-selected so that the system does not present certain types of images, e.g., of genitalia, of morbid conditions, of surgical procedures, etc. (Tags for such imagery can be maintained in the knowledge base, so that images may be filtered on this basis.)

The user interface can also allow the user explore imagery in the database. For example, if the system presents a reference image depicting a leg lesion that is similar to a lesion on the user's leg, the user may choose to view follow-on images of that same reference lesion, taken at later dates—showing its progression over time. Similarly, if the reference lesion was found on the leg of a prior user who also submitted imagery showing a rash on her arm, the current user may navigate from the original leg lesion reference image to view the reference image showing the prior user's arm rash.

Image navigation may also be based on image attribute, as judged by one or more parameters. A simple parameter is color. For example, one derivative that may be computed for some or all of the images in the knowledge base is the average color of a lesion appearing at the middle of the image (or the color of the pixel at the middle of the image—if a generalized skin condition such as a rash is depicted there). The user can query the database by defining such a color (e.g., by pointing to a lesion in user-submitted imagery, or by a color-picker interface such as is employed in Photoshop software), and the software then presents the image in the knowledge base that is closest in this metric. The user may operate a control to continue such exploration—at each step being presented an image that is closest in this attribute to the one before it (but not previously displayed).

Similarly, the user interface can permit user navigation of reference images based on similarity in lesion size, shape, texture, etc.

Hair on skin can be a useful diagnostic criterion. For example, melanoma is aggressively negative for hair; hair is rarely seen from such growths. So hair depictions should be included in the knowledge base imagery.

However, hair sometimes gets in the way. Thus, certain of the processing may be performed using image data from which the hair has been virtually removed, as detailed earlier.

The user interface can allow the user to tap at one or more locations within a captured skin image, to identify portions about which the user is curious or concerned. This information is conveyed to the central system—avoiding ambiguity about what feature(s) in the image should be the focus of system processing. The user interface can allow the user to enter annotations about that feature (e.g., "I think I first noticed this when on my Las Vegas vacation, around May 20, 2013").

Additionally, or alternatively, when the central system receives a user image, and processes it against the knowledge base information, it may return the image with one or more graphical indicia to signal what it has discovered. For example, it may add a colored border to a depicted lesion (e.g., in red—indicating attention is suggested, or in green), or cause an area of the screen to glow or strobe. When this image is presented to the user, and the user touches or otherwise selects the graphical indicia, information linked to that feature is presented, detailing the system's associated findings. A series of such images—each with system-added graphical indicia (e.g., colored borders)—may be rendered to illustrate a time-lapse evolution of a skin condition, as detailed earlier.

Skin is our interface between our body and our world; our interaction with our environment is largely recorded on this thin layer. The present technology helps mine some of the wealth of information that this record provides.

Rainbow Mode

Reference was made to gathering multiple frames of imagery under different, spectrally tuned illumination conditions, such as by using illumination sources (e.g., LEDs) tuned to different wavelengths.

As detailed in cited publication 20130308045 and application Ser. No. 14/201,852, N different spectral illumination sources combine with M different spectral detectors (e.g., the three different color filters overlaying a smartphone photodetector array) to yield up to N*M different sets of image data. From this richness of different image data, a rich set of different features can be discerned.

Those patent applications further detailed how ambient lighting effects can be largely removed, even if the spectrally-tuned illumination amounts to just 10% or so of the total illumination.

In accordance with a further aspect of the present technology, illumination at different spectral wavelengths is provided by illumination from a smartphone screen. One such method captures imagery using a smartphone's front-facing camera (i.e., the camera on the same side of the phone as the touchscreen), instead of the usual rear-facing camera. The field of view captured by the front-facing camera is then illuminated—at least in part—by light from the smartphone screen. This screen is software-controlled to present a sequence of different illumination patterns or colors ("rainbow mode"), during which different frames of imagery are captured.

Smartphone and other screens commonly emit "red," "green" and "blue" light—each with a particular spectral profile. (This profile typically varies from one type of smartphone to another—due to different display technologies, and sometimes varies among smartphones of the same type due to process variations.) Importantly, these spectral profiles never exactly match the red-, green- and blue-Bayer sensor pixel spectral profiles—giving rise to the multiplicative effect noted above.

For example, some "blue" illumination from the display screen will slightly "light up" green Bayer-filtered pixels. "Green" illumination from the display screen will excite all three (R/G/B) Bayer-filtered photosensors. "Red" from the display will excite both red- and green-filtered photosensors. This example gives seven cross-combinations, or "channels," which the cited patent disclosures discuss in great detail, e.g., describing and characterizing how these channels vary in quality and information content. (While there are nine combinations of screen colors and photosensor colors, blue and red are sufficiently remote—spectrally— that the coupling effect is essentially nil.)

OLED displays are coming into widespread use (e.g., the Samsung Galaxy SIII, S4 and S5) and offer increased brightness and wider gamut, compared with previous technologies.

Flexible displays are also beginning to appear commercially. These are attractive to illuminate 3D relief features at close imaging distances, as the display is operated to sweep illumination from one side to the other.

Autostereoscopic displays (commonly including parallax barriers) can also be used, and can create structured illumination.

One illustrative embodiment uses rainbow mode in capturing and processing frames of image data from a user's face. In a particular implementation (which may be called Face-Chek), the motion and/or pose of a smartphone is sensed, and used to switch between data collection and data presentation modes.

As is familiar, the motion and pose of a smartphone can be discerned by reference to data from the phone's onboard accelerometers, magnetometers and gyroscopes—each commonly 3D. (Motion can also be assessed by reference to apparent movement of imagery captured by the phone camera.)

In data collection mode, the user waves the phone around the head (and optionally scalp), capturing frames of imagery with the front-facing camera, from different vantage points. During such motion, the phone screen is displaying a sequence of different illumination patterns/colors. Software analyzes the imagery captured under these various illumination/viewpoint conditions to identify features of potential concern, classify features by type, create longitudinal image sequences illustrating changes in particular features, etc. When the device is thereafter held static by the user for viewing, this information is presented. (This static pose is typically one in which the screen is inclined upwardly, with the base of the screen substantially horizontal, i.e., within ten degrees of the horizon.)

The screen illumination can be of various types. At some update rates, human persistence of vision causes the illumination to seem uniform, e.g., all white. At slower rates, different colors or patterns flash across the screen.

A simple arrangement sequentially displays screens of all-red, all-green, all-blue, in cyclical fashion. In a variant, the phone's "torch" (i.e., illumination flash) is operated in a fourth phase of the sequence, giving four different illumination states.

In another arrangement, solid screen colors are still employed, but this time with combinations of the red/green/blue primaries (yielding what may be termed cyan, magenta and yellow).

In some arrangements, the transitions between colors are abrupt. For example, a red screen can be maintained for a sixth of a second, and then switch to blue for the next sixth of a second, etc. In other arrangements, the transitions are blended. For example, a displayed solid color may be updated thirty times a second. At a first frame, red is presented. At the second frame, 20% of the red pixels are changed to green. And at the third frame, 20% more of the red pixels are changed to green. A seemingly-continuous smear of colors results (but is actually 15 different colors. Twice a second the display is all-red. Ditto for all-blue and all-green.

Capture of image frames by the camera is synchronized to the different frames of illumination. In the example just-given, the camera may capture six frames of imagery per second (i.e., two with all-red illumination, two with all-blue illumination, and two with all-green illumination).

Skin topology features are best revealed by illuminating the skin obliquely, at various different angles. This can be done by operating the screen to present illumination from different parts thereof, at different times. The rest of the screen can be kept dark (black).

Figure 7:
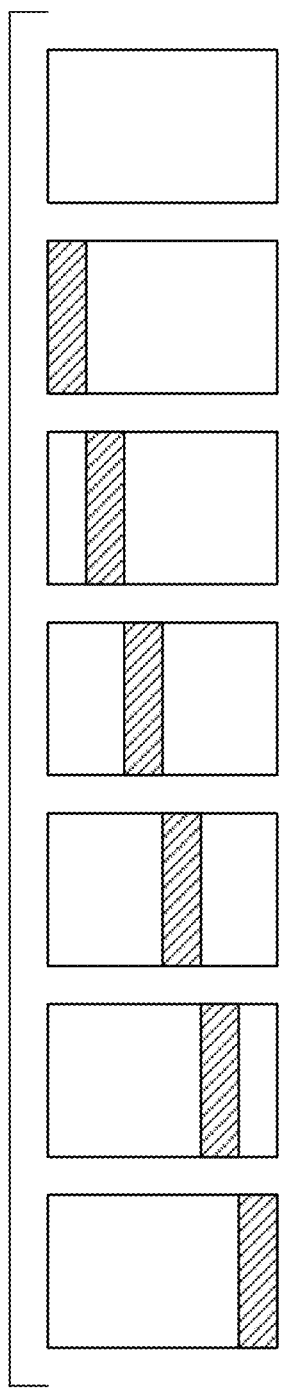
FIGS. 7, 8 and 9 detail sequences of smartphone screen displays that provide illumination of different spectral characteristics, from different positions relative to the smartphone camera.

One such arrangement is shown in FIG. 7. The display screen at the top of the figure is all-dark (black). After a fixed interval a colored band appears along the left edge of the screen. A further interval later it shifts one band-width to the right. In similar fashion the color band marches across the screen. (While six discrete steps are illustrated, a greater or lesser can be used.)

After the colored band has finished its march across the screen, a dark screen is then presented, followed by a similar march of a band of a different color.

In some embodiments, the sequence of colors (e.g., of the FIG. 7 bands) is sequential, e.g., red, green, blue (or red, green, blue, cyan, magenta, yellow, etc.). In others, the sequence of colors is random.

Likewise with the FIG. 7 progression of the colored band from left to right. In some arrangements this pattern is repeated, with different colors. In others, the direction of the band's movement is changed from one cycle to the next. For example, after the red band of FIG. 7 has marched to the right of the screen in one cycle, the next cycle may have a band of color march from the top to the bottom. Or from the right to the left. Or from the bottom to top. Again, the sequence can repeat, or random directions and/or colors can be used.

Figure 8:
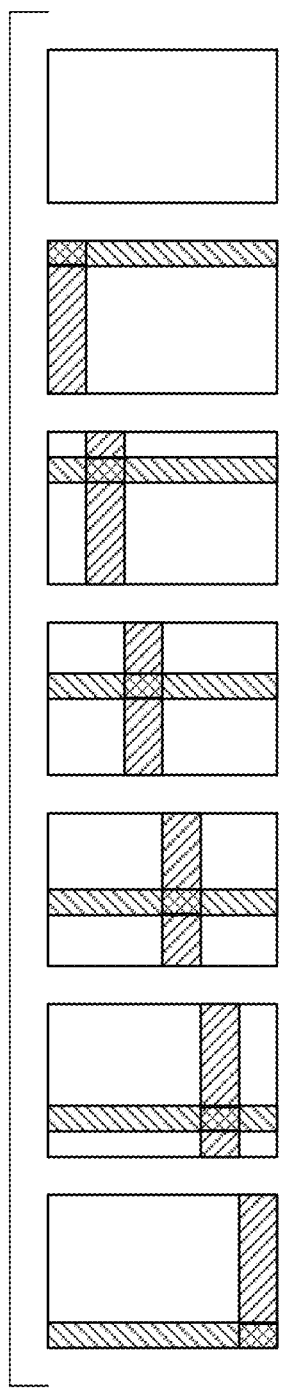

FIG. 8 shows a variant in which two bands—of different colors—move across the screen. As in the arrangement just-described, the color of the horizontal band in different cycles can follow a repeating pattern, or it can be selected randomly. Similarly with the direction of the horizontal band's movement (top-to-bottom, or bottom-to-top). Likewise with the vertical band.

Figure 9:
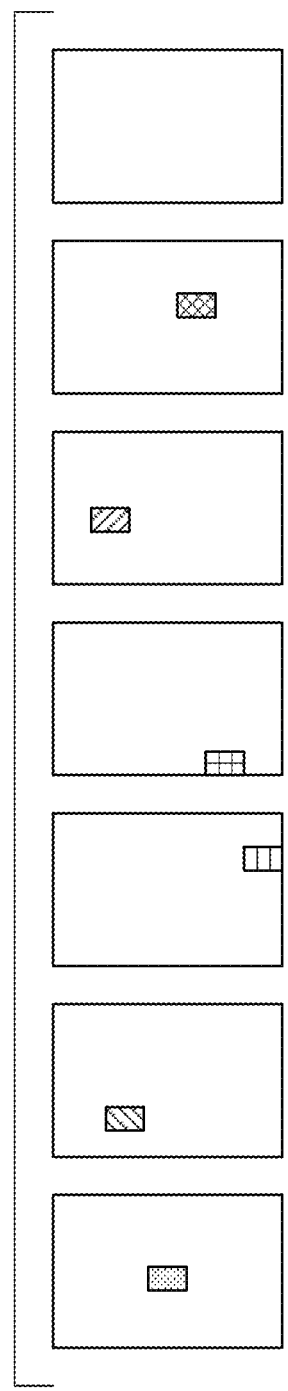

FIG. 9 shows yet another variant, in which blocks of different colors appear at different positions on the screen. As before, the sequence of colors, and positions of the blocks, can follow a repeating pattern, or either/both can proceed in a random sequence.

(In this and other embodiments discussed herein, the device can be an iPhone 5, which has a display that is four inches in diagonal measurement, and has a 1136×640 pixel resolution, i.e., 326 points per inch.)

Figure 10:
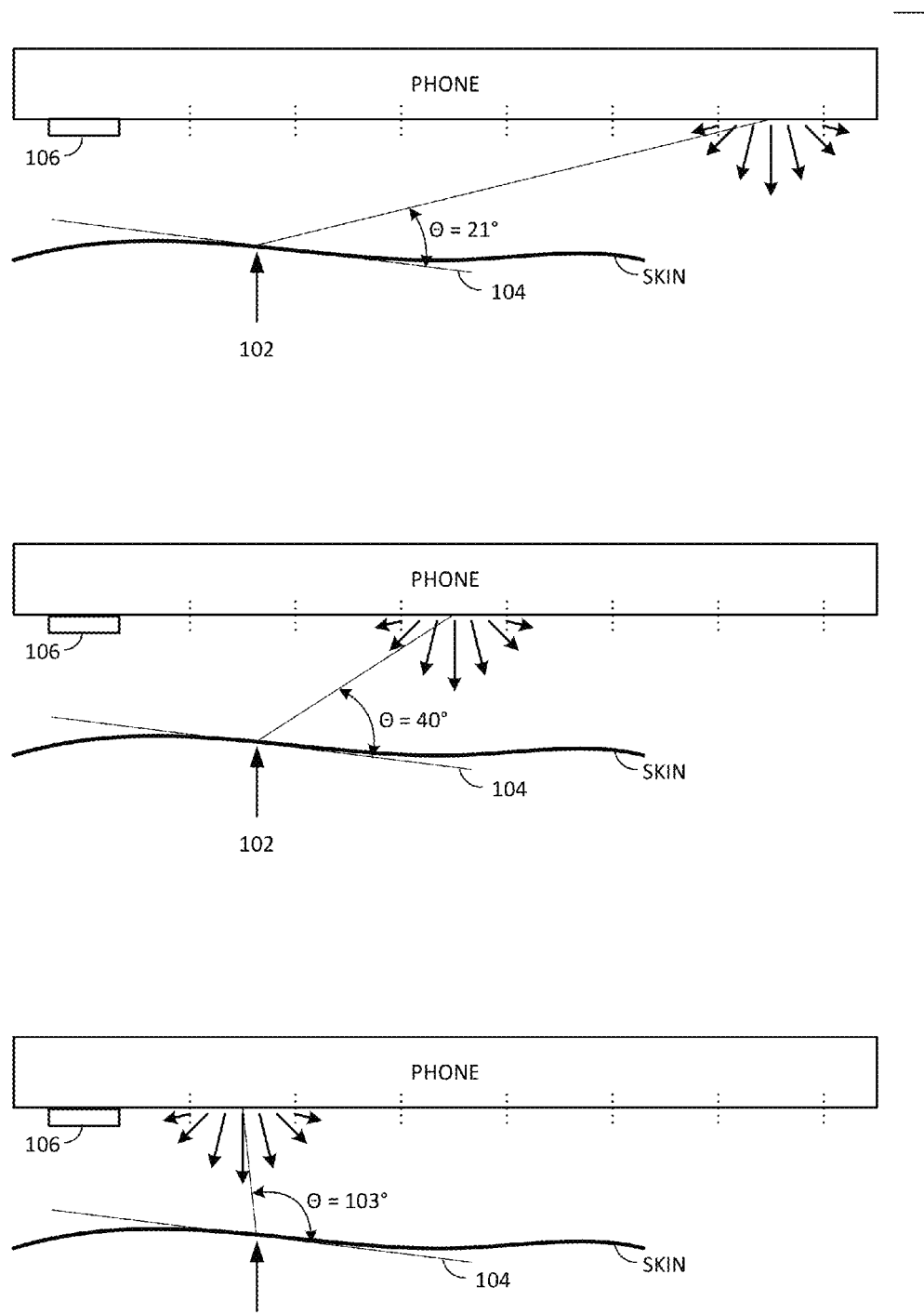
FIG. 10 details how light from different parts of a smartphone screen display illuminates a feature on a skin from different angles.

FIG. 10 further considers certain aspects of the illumination geometry. At the top of the figure, a color band is displayed at one end of the smartphone screen. Light from this band illuminates a location 102 on the skin at an angle of 21 degrees (relative to a tangent 104 to the skin surface).

A few instants later, the band has moved to near the middle of the screen, as depicted in the middle of the figure. Here, light from this band (which may now be of a different color, or not) illuminates the skin location 102 at an angle of 40 degrees.

A few instants later, the band has moved to hear the opposite end of the screen, as depicted in the bottom of FIG. 10. Here, light from this band illuminates the skin location at an angle of 103 degrees.

As before, the phone captures a frame of imagery under each of these different illumination conditions, using a camera 106.

It will thus be recognized that the FIG. 10 arrangement collects imagery of skin location 102 as illuminated from a variety of different angles. If the color of the band changes as it marches across the display, such arrangement collects imagery of the skin location with illumination that is diverse both in angle and spectrum.

While the phone is stationary in FIG. 10, in actual practice, the phone may be moved by the user to different positions relative to skin location 102 while the color band marches across the display screen. Thus, in some embodiments, imagery is captured having diversity in illumination angle, illumination spectrum, and viewpoint.

(To fit three illumination scenarios in the FIG. 10 illustration, the phone is depicted as closer to the skin than may generally be the case. A more typical imaging distance is 4-6 inches.)

The oblique illumination afforded by colors presented on different parts of the screen, together with motion that moves the camera to different viewpoints, helps in revealing millimeter-scale 3D profiles of the skin. Such profile information can aid in classifying certain skin conditions, e.g., dryness, scaliness, age wrinkles, sunburn, etc.

By producing a sequence of, for example, 30 image frames over a one second period, where, for example, 10 different states of rainbow illumination were occurring over that one second period, an information diversity situation is created that goes beyond just the spectral combinations of the display RGB and the sensor RGB; illumination angle effects are now also included in this large gathering of imagery data. As is well known in machine learning and the wide field of classification of objects, it may not always be possible to analytically understand this larger complexity represented in the data. However, the very existence of this extra complexity will allow for higher dimensional discrimination of one class of "thing" over another class of "thing." In the case of this technology and skin, this can involve the simplest of questions such as "is this skin drier or more moist than that skin?" The way this is done is through classic training, where known samples of drier skin, and known samples of more moist skin, all get sampled via these rainbow illumination ways, and their resultant higher dimensional differences and unique characteristics all get "trained in" to this otherwise incomprehensible set of data. Modern classification approaches routinely deal with data vectors having 100 or even 1000 or more dimensions of related information. A patch of skin having been illuminated with all these spectral combinations and from these various spatial directions can easily give rise to dozens or hundreds of bundled data attributes at millimeter by millimeter scales represented by the pixels of the camera. Spatial derivatives of these data, e.g., how does the "red light from the left pixel datum" change from this pixel to ten pixels over, innately carry discrimination information between a new red rash that might be lumpy versus the less lumpy nature of a hickey, to use a deliberately out-there example. Thus, perhaps, boyfriends and girlfriends can quickly check for any youthful infidelities as but one tiny application for rainbow-derived data captures.

Sunburn analysis is another application where spatial-spectral rainbow diversity can enrich the identification and discrimination power of captured imagery. The emergence of even very small blistering, perhaps very difficult to see even with a magnifying glass, will nevertheless exhibit different far-field optical characteristics over, say, non-blistering but nevertheless still-painful lesser degree burns. Dryness detection of skin was already mentioned, whereby with rainbow diversity, it is possible to build up a "scaling system" of degrees of dryness, such that users can make their own choices about when and when not to apply various skin moisturizers. The aging of skin is another area where there are a vast number of people interested in better understanding not simply what to do about aging skin, but to understand the state of their own skin and to understand how they might be able to treat and track the various remedies they employ in the battles against aging. The rainbow spectral-spatial diversity here again can provide a richer set of direct empirical samplings of the intricacies of wide varieties of skin conditions which, after all, derive from a very complicated three-dimensional structure, namely human skin.

The general principles of shining spectrally shaped light from some angle in space can of course be accomplished by LED's that are somewhat collimated or even tunable lasers. The broadest principle being taught here is that though the microbiology of specific skin conditions or skin topologies may be too complicated to create recognizable patterns from this diversity of lighting angles and spectra, it nevertheless can still be measured and used to discriminate condition A from condition B, or even stages of progression of some singular condition. As machine learning practitioners understand, the resulting data vector populations disperse themselves in higher dimensional vector spaces in such a way that by training on known condition types, generating signatures of the populations a la SVM types of boundary conditions on these types, then comparing unknown test cases against these populations can be a method for discriminating conditions which otherwise might look nearly identical to a normal color camera not employing these rainbow sampling techniques.

(Additional information regarding acquiring data from multiple-viewpoint imagery, e.g., to detail surface attributes, is detailed in applicant's publication 20080112596.)

Audio, Etc.

In accordance with other aspects of the present technology, audio (and other physiologic data) is collected and used in manners like the skin imagery herein.

For example, one particular embodiment employs regression analysis on a set of audio data to characterize false conclusions that should not be drawn. (Culling the false helps in identifying the truth.) Another compares extracted features against templates of "normal" features, to identify anomalous signals that should be reviewed by a qualified physician. Patent publications 2002085724, 2005078533, 2008046276, 2008062389, 2010045210, 2011009759, 2011021939, 2011096820, 2011076328, 2012043018, 2012090303, 2013016584, 2013061484, 2014012149, WO0209396, and WO13156999 detail a variety of technologies useful in collecting and processing physiological sound information, which are suitable for use with the arrangements described herein.

Among the different audio data collection arrangements are bell and diaphragm type pick-ups, acoustically coupled to one or more microphones. Such a pickup can be provided in a separate unit—coupled to a portable device (e.g., smartphone) by wire (e.g., employing the headphone/mic jack) or wirelessly (e.g., employing Bluetooth). Alternatively, such a pickup can form part of the portable device, either permanently, or by an accessory unit that is removably attached to the device body. An example of the latter is a downwardly-opening funnel-like member (e.g., made of plastic) that friction-fits over the lower inch or half-inch of a smartphone body, channeling sounds from the wide end of the funnel up to the microphone(s) normally used for telephone communication.

In other arrangements audio sensing can be done by worn microphones. In some embodiments, one or more microphones are provided in a band (e.g., a wrist- or waist-band) worn by a user (or worn by a clinician, for probing a user). In others, acoustic sensors are integrated in clothing or other garments. By positioning microphones at different locations on the body, the spatial origins of different sounds can be better determined, aiding their diagnostic significance. In still other arrangements, head-worn microphones can sometimes be employed (e.g., Google Glass-like arrangements).

To reduce the influence of spurious (i.e., non-physiologic) audio found in the ambient environment, one or more other microphones can be employed to sense the ambient audio, so it can be removed from the sensed physiologic audio, using known noise cancellation techniques. (Smartphones are increasingly provided with multiple microphones; one or more of these can be used to enhance the sensed physiological signals.)

A variety of diagnostically relevant acoustic signals can be sensed. These include heart sounds and other cardiovascular sounds (including murmurs, bruits, and other blood flow noises), lung and other respiratory sounds (including crackles, rales, rhonchi, wheezes, coughs, snoring and other air flow noises), bowel and digestive sounds, joint noises (e.g., pops and creaks), as well as speech and other vocalizations.

In gathering data for analysis, and for comparison against reference data, a variety of processing techniques can be employed.

One processing technique characterizes and strips-out positioning sounds, e.g., when a microphone is moved and rubbed against a person's skin, before settling at a final position for data collection. A classifier can be trained to recognize such positioning sounds, so that they are not used in diagnostic processing.

Another processing technique is noise-cancellation, e.g., as noted above, and in certain of the cited patent documents. A suitable wavelet-based denoising arrangement is detailed in Messer, et al, Optimal Wavelet Denoising for Phonocardiograms, Microelectronics Journal 32.12, pp. 931-941 (2001). Spectral filtering can also be employed, when same is desired based on measurement context.

Other signal processing techniques useful with physiologic signals may be broadly classified into the following overlapping areas:
1. Prediction based techniques—useful for cardiovascular and respiratory sounds that have a predictable (repetitive) structure
    a. Prediction error can be useful in detecting abnormalities in heart beats and also in isolating noise-like signals, e.g., a murmur, in the presence of a stronger heart beat signal.
    b. Transient signals are not easily predictable either. So, in analyzing a wet cough signal, there may be a transient component which will be present in dry cough but in wet coughs there will also be a predictable component which will be absent in the dry coughs (based on an excitation model for coughs).
2. Time-frequency techniques—FFTs, Spectrograms etc.
    a. Spectrograms can be analyzed for high frequency vs low frequency signals—noise-like signals have higher frequency content—air flow sounds, murmurs etc.
3. Transient analysis—short frame analysis
    a. Pops and crackles are transient signals and they can be detected/analyzed using short frame audio analysis
    b. Energy envelope is also useful in transient signal analysis
4. Fingerprinting techniques
    a. With enough training examples, audio fingerprinting features and matching techniques from the field of music and video recognition can work for physiologic sounds. (Examples of audio fingerprinting and matching are detailed in patent publications 20070250716, 20070174059 and 20080300011 (Digimarc), 20080276265, 20070274537 and 20050232411 (Nielsen), 20070124756 (Google), U.S. Pat. No. 7,516,074 (Auditude), U.S. Pat. Nos. 6,990,453 and 7,359,889 (Shazam), 20050141707, 20050259819, and 20060075237 (Gracenote), and U.S. Pat. No. 8,656,441 (Cox).)
    b. One example of a fingerprinting based diagnosis is to collect "healthy" audio data (when the patient is healthy) and then analyze any deviation from the signatures or fingerprints of this healthy data to determine pathologies in future diagnostic examinations.

Such processing can provide a variety of "features" that can be compared with reference data in assessing whether a signal is normal or anomalous (and, if the latter, used to help identify what the anomaly is—or is not).

One approach is to use an auto-regressive model to parameterize the sensed sounds. This is the approach employed, e.g., by Harma et al in Time-Varying Autoregressive Modeling of Audio and Speech Signals, Proc. of the EUSIPCO, pp. 2037-2040, 2000.

Another approach uses features including the MFCC (Mel-Frequency Cepstral Coefficients) and PLP (Perceptual linear predictor) that are used in the automatic speech recognition field.

Coughs, snores, bruits, and other isolatable or cyclically recurring sounds can be parameterized, in one respect, by identifying the time interval over which a threshold (e.g., 80%) portion of the spectral energy is expressed, and the smallest frequency bandwidth (characterized by low and high frequencies) within which a threshold (e.g., 90%) portion of the spectral energy is expressed. (These low and high frequency bounds can also independently serve as useful features.)

A large number of other parameters and features can similarly be derived from a spectrogram of the audio, as illustrated by the following Table 1, adapted from the thesis by Glaeser, Analysis and Classification of Sounds Produced by Asian Elephants (Elephas Maximus), Portland State University, 2009. (In this table, the just-noted features are essentially features M5, M6, M3 and M4, respectively.)

TABLE 1

| Parameter | Units | Description | Type |
|---|---|---|---|
| M1-M6: Feature box | | | |
| Start Time (M1) | sec | Lowest time index in bounds that encompass the inner 90% of the signal strength in the time envelope. | temporal |
| End Time (M2) | sec | Highest time index in bounds that encompass the inner 90% of the signal strength in the time envelope. | temporal |
| Lower Frequency (M3) | Hz | Lowest frequency index in bounds that encompass the inner 90% of the signal strength in the frequency envelope. | frequency |
| Upper Frequency (M4) | Hz | Highest frequency index in bounds that encompass the inner 90% of the signal strength in the frequency envelope. | frequency |
| Duration (M5) | sec | Width of feature box: M2-M1 | temporal |
| Bandwidth (M6) | Hz | Height of feature box: M4-M3 | frequency |
| M7-M14: Central values and variation<br>Uses measures that do not assume normality: median, quartile ranges, quartile skewness, concentration. | | | |
| Median Time (M7) | sec | Time at which 50% cumulative signal energy is reached.<br>(Measured relative to start of sound, so M7 was calculated as M7new = M7-M1) | temporal |
| Temporal Interquartile Range (M8) | sec | Concentration of a sound around the median time (M7) measured as the duration of the interquartile range of signal energy (Q3-Q1).<br>Counts energy going forward and back from the median time (M7).<br>Q3 = median + 25% of signal energy<br>Q1 = median-25% of signal energy | temporal |
| Temporal Concentration (M9) | sec | Concentration of a sound measured as the time span encompassing loudest 50% of time envelope values.<br>Counts energy from the loudest parts down towards the smallest parts regardless of where the parts occur in time. | temporal |
| Temporal Asymmetry (M10) | none | Skewness of energy along time axis within interquartile range (−1.0 to 1.0) | temporal |
| Median Frequency (M11) | Hz | Frequency at with 50% cumulative signal energy is reached.<br>More stable than extreme values of LowerFreq and UpperFreq in varying noise conditions. | frequency |
| Spectral Interquartile Range (M12) | Hz | Concentration of a sound around the median frequency (M11) measured as frequency range of interquartile range of signal energy (Q3-Q1).<br>Counts energy going forward and back from the median frequency (M11).<br>Q3 = median + 25% of signal energy<br>Q1 = median-25% of signal energy | frequency |
| Spectral Concentration (M13) | Hz | Concentration of a sound measured as the frequency span encompassing loudest 50% of frequency envelope values.<br>Counts energy from the loudest parts down towards the smallest parts regardless of where the parts occur in time. | frequency |
| Frequency Asymmetry (M14) | none | Skewness of energy along frequency axis within interquartile range (−1.0 to 1.0) | frequency |
| M15-M20: Peak intensity | | | |
| Time of Peak Cell Intensity (M15) | sec | Time of single loudest spectrogram cell.<br>Time of the cell containing the peak intensity.<br>(Measured relative to start of sound, so M15 was calculated as M15new = M15-M1) | temporal |
| Relative Time of Peak Cell Intensity (M16) | % | Relative time of peak intensity (M15/M5) | temporal |
| Time of Peak Overall Intensity (M17) | sec | Largest value in time envelope, which is the largest vertical sum of the spectrogram over all frequencies. Time of the peak intensity in the trimmed time envelope.<br>(Measured relative to start of sound, so M7 was calculated as M17new = M17-M1) | temporal |

TABLE 1-continued

| Parameter | Units | Description | Type |
|---|---|---|---|
| Relative Time of Peak Overall Intensity (M18) | % | Relative time of peak intensity (M17/M5) | temporal |
| Frequency of Peak Cell Intensity (M19) | Hz | Frequency of cell containing the peak intensity. | frequency |
| Frequency of Peak Overall Intensity (M20) | Hz | Frequency of peak intensity in the trimmed frequency envelope. | frequency |
| M21-M24: Amplitude and frequency modulation (variation of amplitude and frequency over time) | | | |
| AM Rate (M21) | Hz | Dominant rate of amplitude modulation. Frequency of the maximum rate in the power spectrum of the trimmed time envelope. | amplitude |
| AM Rate Variation (M22) | Hz | Variability of amplitude modulation measured as the width of peak at M21-6 dB. Values are discretized because at 6 dB down from the peak, the widths may be a only a few bins wide so the values are integer multiples of the bin width. | amplitude |
| FM Rate (M23) | Hz | Dominant rate of frequency modulation. Frequency of the maximum rate in the power spectrum of the trimmed frequency envelope. | frequency |
| FM Rate Variation (M24) | Hz | Variability of frequency modulation measured as the width of peak at M23-6 dB. (How much the rate of change varies, may be related to inflections and steepness of upsweeps and downsweeps) | frequency |
| M25-M28: Fine features of harmonic structure, shifts in periodicity, direction of frequency change, rate of change in frequency | | | |
| Cepstrum Peak Width (M25) | Hz | Harmonic structure Average width of peaks (harmonics) in power spectrum. Peak width is measured at 6 dB down from maximum value. At 6 dB down from the peak, the widths may be a only a few bins wide (like M22 and M24), but M25 is an average of integers so the values are not discretized. Narrow peaks means narrowband/tonal harmonics. | structure |
| Overall Entropy (M26) | Hz | Entropy, shifts in periodicity Distribution of energy across frequency blocks in a given time block. Shift from periodicity and linearity to chaos. Change in noisiness v. tonality. | structure |
| Upsweep Mean (M27) | Hz | Direction of frequency change Measures how much the frequency increases. Average change in median frequency between successive time blocks, weighted by total energy in the block. Inflection points with rising and falling frequencies throughout call result in a low M28 (closer to 0) compared to a consistent directional change. Measure is weighted to emphasize contribution of louder signal components. M27 <0 means frequency is decreasing. | frequency |
| Upsweep Fraction (M28) | % | Rate of directional frequency change Counts the number of times the frequency content increases. Fraction of time in which the median frequency in one block is greater than in the preceding block, weighted by total energy in the block. Indicates how much of the call has a directional change in the frequency. Inflection points with rising and falling frequencies throughout call result in a high M28, just as a consistent directional change. Measure is weighted to emphasize contribution of louder signal components. M28 always positive. | frequency |
| M29: Signal strength | | | |
| Signal-to-Noise Ratio (M29) | dB | Signal to noise ratio within the sampled sound. Ratio of the signal power (loudest cell) to the noise power (power of cell at $25^{th}$ percentile). Cells are ranked low to high and the cell at the $25^{th}$ percentile represents noise. ($25^{th}$ percentile is used because the sound likely takes up less than | amplitude |

TABLE 1-continued

| Parameter | Units | Description | Type |
|---|---|---|---|
| | | 75% of the total spectrogram cells.) Measurement assumes that the within the annotation box at least 25% of the cells are without a focal signal. | |

An ensemble of some or all of the twenty-odd parameters just detailed (as well as others) can be computed for a sensed sound, and compared with reference data to discern similarity to (or deviation from) reference ensembles of parameters—either individually, or in statistical fashion (e.g., a particular respiratory sound is two standard deviations away from what may be regarded as the median for subjects of similar age, weight and gender). The reference data may have been collected solely from a single person over time (e.g., a longitudinal record of earlier-sensed physiologic sounds from that person), or from a collection of individuals—commonly a grouping that is demographically similar (e.g., 40-50 year old healthy males weighing between 170 and 190 pounds).

One particular example concerns detection of bruits in a major artery. This can be predictive of a stroke. The user may periodically place a phone or other audio sensor over the femoral (or carotid) artery. Five or ten seconds of collected sounds can be converted into features, as described above, and these features can be compared with features derived from known bruits sounds. If the comparison indicates similarity beyond a threshold degree (e.g., a feature distance below a threshold value), the user can be advised to have their arteries checked for occlusion.

Patent publications 20070265508, 20110021939, 20110196820 and 20130261484 detail a variety of other ways that biometric signals can be processed, e.g., for comparison.

As noted, speech and other vocalizations also have diagnostic value. Pitch, timbre, rhythm, pace, and volume (and variation in same), are some of the vocalization attributes that can be monitored. Changes from historical norms are sometimes symptoms or precursors of different conditions, such as depression, stroke, alcohol poisoning, respiratory illness, etc.

Depression, for example, is often accompanied by slower and quieter speech, with reduced variation in pitch. Respiratory illness can be discerned from lower-pitched speech, with rougher/coarser timbre (e.g., due to swollen vocal cords).

Coughs may be characterized by characteristics such as frequency and type (e.g., a dry cough—staccato in nature, with a sharp onset, short duration and dominant high frequency components; and a wet cough—commonly the opposite). A user's cough may be matched to prototypical coughs (the user's own, or others) on a "fingerprint" basis, such as employing a collection of the features detailed in Table 1, above. A user's current cough may be matched to a previous episode of user coughing, on a prior date. Recalling other physiologic information from around that prior date may presage upcoming symptoms, e.g., elevated body temperature, runny nose, etc.

Finer classification of coughs can be achieved with a sufficiently large collection of reference data. A wet cough originating from irritation of the upper airway (e.g., mucus in the large bronchi) exhibits one set of features, whereas a cough originating from the lower airway (e.g., pneumonia in the lungs) exhibits a different set of features. A distance measure can be employed to assess whether the set of features characterizing a user's cough are closer to the former or the latter; the relative distances provide a confidence metric. More sophisticated classifier arrangements can also be employed.

(The audio characteristics of coughs—most especially pitch—depend, in part, on dimensions of the acoustical bodies involved. Thus, in selecting reference data for comparison, it is desirable to pick sounds captured from persons of the same gender, and about the same age, weight, height and—if known—lung capacity. If such a closely-matched set of reference data is not available, the feature matching operation can rely less on absolute pitch-related features, and more on other features.)

An alternative implementation to explicit distance measures is provided by classical machine learning methods. In this case, a database is collected, consisting of appropriate audio captures, together with tag data indicating presence of the specific types of coughs to be identified. The audio is then processed to provide a rich set of features, which form the input to a machine learning paradigm (e.g. a Support Vector Machine (SVM), or an Artificial Neural Network (ANN). Additionally, the database should include metadata to indicate gender, age, height, weight, etc. This metadata is then provided as additional features to be learned. Thus, the learning process automatically takes these variables into account (to the extent to which the database is varied enough to span this metadata space). In the case of an ANN, a single network output may be provided for each cough type to be recognized; a specific cough type may then be identified by choosing the cough type with the strongest response over a predetermined threshold (assuming exclusivity among cough types). In the case of an SVM, coughs may be classified into many (>2) classes, based on the design of several binary classifiers. Two popular methods are "one vs. rest" and "one vs. one."

Medical practice, to date, has tended to classify coughs only in gross senses (e.g., wet/dry). With the present technology, and with widespread collection of coughing sounds, more nuanced distinctions may be found in coughs—allowing, e.g., the causation of a particular cough to be more accurately determined. Thus, the present technology can help reveal previously undiscovered knowledge.

Likewise, analysis of a large corpus of audio physiologic data (and derivatives), and correlation with diagnostic ground truth (e.g., evaluations from physicians), can find small clues that reliably indicate big problems. For example, it may be discovered that a consequence of carbon monoxide poisoning is a particular change in the high frequency component of inhalation sounds sensed from the lower lungs. Similarly, it may be discovered that certain types of strokes are commonly foreshadowed by a change in the pronunciation of diphthongs (e.g., as in "oil"). When user audio and diagnostic information becomes available for analysis in a Big Data sense, a universe of such statistically-reliable correlations are likely to be found. Thereafter, a user's portable device can monitor sensed sounds (and other sensed physiologic data) for such clues (e.g., comparing current sound signals with historical data), and alert the user to maladies—both present and upcoming—that the user may not recognize.

Collections of reference audio data are not yet as readily available as, e.g., reference collections of mole imagery. However, such reference information can be crowd-sourced in the same manners as for imagery. Since audio information is straight-forward to collect in continuous fashion, the smartphone (or other device) of each user can serve as a collection agent, and forward large amounts of audio data (or features derived from the audio data) to a cloud repository in a relatively short time.

Ground truth diagnostic data concerning such audio is harder to compile. Patients commonly don't consult physicians concerning unfamiliar coughs (as they might for unfamiliar moles); only if a person's respiratory symptoms become severe is a physician usually involved. Moreover, pulmonary, bowel, and other audio signals escape the user's normal attention, so irregularities in those signals normally don't prompt professional consultations.

Still further, physicians do not normally record patients' physiologic sounds—unlike the practice of photographing patients' skin conditions. Rather, a physician typically just listens to a cough, or listens to sounds heard through a stethoscope, and offers a diagnosis based on what was just heard. However, with the proliferation of electronic medical records, and the movement towards data driven medical protocols and auditable outcomes, the digital collection and archiving of sensed patient data—including coughs, stethoscope sounds, and all manner of other physiologic signals (e.g., anatomic imaging by various radiological techniques)—is expected to become more widely practiced. Thus, electronic medical records may soon provide both captured data and associated diagnostic information, which can serve as ground truth in connection with the present technology, eventually leading to the reliable statistical knowledge that comes with Big Data.

(In other arrangements, the physician's medical records are not employed. Instead, a user may enter data in a personal life-log, recounting a visit to the doctor, together with the doctor's diagnosis. Such information is then associated with audio that is life-logged from the user—before and/or after the doctor visit. A small corpus of training audio, and associated diagnostic conclusions, are also available from medical schools, where they are used in training new physicians.)

While the focus of this discussion has been on audio, it will be recognized that the same principles can be applied to collection and processing of other physiologic information. Without limitation, this includes blood pressure and blood sugar, electric signals from the heart, brain and nervous system, etc. A range of different sensors can be employed, including electric, vibration, optical, stress, strain, chemical, etc.

A variety of multi-sensor, phone-based medical devices are known from the prior art, e.g., as shown in patent publications 20050124375, 20090030286, 20100056880, 20120059271 and WO2013156999. Scanadu has publicized its Scout and Scanaflo offerings, which can sense temperature, blood pressure, heart rate, oximetry, ECG, heart rate variability, stress, and urine chemistry—many using optical techniques. (Patent publications WO2013066642, WO2013116316, WO2013116253, and WO2014025415 detail certain of the Scanadu technologies.) Azoi, Inc., similarly has publicized its upcoming Wello product, in which sensors are integrated in a smartphone case, and communicate by Bluetooth to a health tracker app on the phone. The app logs heart rate, blood pressure, blood oxygen, respiration, heart rate variability (as an indicator of stress), ECG, temperature, and lung function (with an accessory spirometer).

Automated cough detection and rudimentary signal analysis is the subject of Larson, et al, Accurate and Privacy Preserving Cough Sensing Using a Low-Cost Microphone, Proc. of the 13$^{th}$ Int'l Conf on Ubiquitous Computing, ACM, 2011, and Birring, et al, The Leicester Cough Monitor: Preliminary Validation of an Automated Cough Detection System in Chronic Cough, European Respiratory Journal 31.5, pp. 1013-1018 (2008).

Many embodiments of the present technology advantageously consider multiple physiological signals together, for their diagnostic relevance (e.g., an ensemble of plural signals that co-occur in a relevant manner) or for signal processing purposes. For example, in processing signals having a repetitive structure (e.g., many respiratory and circulatory signals), the signals from different repeating waveform periods can be averaged, combined, correlated, compared, filtered or windowed. While the periodicity can be inferred from, e.g., the audio itself, it can sometimes be independently determined. For example, for blood flow sounds, the periodicity can be determined by reference to electric signals sensed from the heart (e.g., the QRS complex, or the T wave of an EKG signal). Thus, timing derived from electric signals can be employed in processing acoustic signals.

It will be understood that sometimes the body can be stimulated at one location with an audio signal or pressure waveform, and the signal can be sensed at another location, to discern information about the intervening transmission medium. Fluid behind the tympanic membrane can be sensed in this fashion. Dehydration can also be so-indicated, based on the degree to which the skin is stretched or loose. Enlargement of the liver and constipation can also be discerned in this way, by detection of a solid (dense) mass under the skin.

Percussion analysis is used by physicians in clinical diagnosis for the abdomen and thorax. The resonance properties of the acoustic waveform resulting from the acoustic stimulation can be examined to classify the sounds as normal, hyper-resonant, impaired resonant or dull. Formant analysis of the captured waveforms yields information about acoustic resonance. Information about associated symptoms (e.g., pain) can be used in conjunction with the captured acoustic signals for automated analysis.

While "sounds" and "audio" commonly refer to human-perceptible stimuli, these terms are used herein to include stimuli that may be below, and/or above, the frequency range of human hearing. MEMS microphones used in many smartphones, and many of the speakers, are operable well outside of the human hearing range. Thus, some embodiments of the technology sense data, e.g., in the ultrasonic range. (Stimulus can also be provided in this range.) The ability of the user device to sense sounds outside the range of human hearing provides capabilities beyond those of unassisted physicians.

For example, with an ultrasonic-capable microphone and speaker, a smartphone may serve as a rudimentary echocardiogram device—stimulating a portion of the body with ultrasonic audio, sensing the phase (and amplitude) of the returned signals, and presenting resultant information on the display screen. By such arrangement, a variety of at home testing/monitoring can be conducted, including detection of certain dilated aorta conditions.

In classifying sensed physiologic data, hidden Markov models, artificial neural networks, and deep neural networks can be employed, borrowing techniques known from the field of pattern recognition. (Hidden Markov models are also known in analysis of animal vocalizations; see Ren et al, Framework for Bioacoustic Vocalization Analysis Using Hidden Markov Models, Algorithms 2, No. 4, pp. 1410-1428, 2009.) Classification trees, support vector machines, and other discriminatory classification techniques can also be employed. Such classifiers use feature data from physiological acoustic data and known diagnoses as training sets.

The ensemble of parameters (or features) outlined above can also be used in unsupervised learning methods to learn complex, non-linear models of many-dimensional underlying data. Examples of such techniques include deep belief networks and sparse coding. (See, e.g., Raina, et al, Large-Scale Deep Unsupervised Learning Using Graphics Processors, Int'l Conf. on Machine Learning, Vol. 9, 2009.) These techniques are suitable for high-dimensional input data and can enable inference of latent variables or conditions. Such deep learning approaches can unearth new patterns or diagnostic tools using large numbers (even millions) of collected samples of various physiological acoustic data. A valuable input to these techniques is the change of physiological acoustic data over time. Such data can be obtained by sensing the physiological phenomenon (e.g., heartbeats, coughs, murmurs, etc.) at different times over multiple days (or longer intervals).

Note that acoustic features can be combined with other available diagnostic information (pulse rate, temperature, blood pressure, etc.) and be provided as input to automated learning and classification methods (both supervised and unsupervised).

Other Arrangements

A health app according to one implementation of the present technology employs a wearable network of sensors to capture and log a history of physiologic signals, and refer related information to one or more remote processors (e.g., "the cloud") for large scale systemic analysis.

Many existing sensors can be employed in such an arrangement. One is a wrist-worn activity tracker, such as the Fitbit Force, Basis, Larklife, Jawbone UP, and Nike Fuelband products. As is familiar, various sensors in these devices sense heart rate, temperature, perspiration (commonly based on skin conductivity), and movement (e.g., based on accelerometer, magnetometer, or gyroscope sensor data). From these data, others can be derived, including calorie consumption and sleep stage.

Another type of sensor is a belt or strap, worn across the chest, waist or belly (typically horizontally, but alternatively vertically or diagonally), which can monitor these same parameters, as well as respiration, dimension (e.g., chest/waist/belly circumference), and body sounds. (Obesity seems better gauged by waist- or belly-to-height ratio, rather than weight-to-height ratio.) A band on the upper arm (e.g., across the bicep) or leg/thigh can also be employed, as can sensors deployed around the neck (e.g., in a necklace form) or finger (e.g., in ring form). Many such sensors can be concealed under clothing Blood pressure, blood chemistry, skin imagery data, EKG, EEG, etc., can also be sensed. As noted, some of the sensors can be integrated into worn clothing.

Some sensors can be responsive—in part—to stimulus introduced into the body, such as a small electrical current, audio, vibration, etc. For example, electrical conductivity between two points on the body depends on the amount of intervening fat, muscle and water, as well as the skin contact resistance (which varies with perspiration). Some systems for measuring body composition involve a user standing on two electrical pads, to sense electrical resistance; less resistance indicates less body fat, and a lower body fat percentage.

Audio, vibration, alternating current, and radio beamforming arrays can used—either of emitters (e.g., piezoelectric actuators) or receptors (e.g., MEMS microphones), and employed in conjunction with one or more complementary receptors/emitters on another part of the body, to probe and localize characteristics (e.g., density, electrical conductivity, etc.) of the intermediate body mass, using phased array/synthetic aperture techniques known from other disciplines. (1D arrays can be used, or 2D; the sensor spacing can be spatially regular or stochastic.) By such methods, for example, the origin of a particular respiratory sound can be localized to the upper or lower lung, or to the trachea. Similarly with a murmur or other blood flow sound. (Some murmurs are abnormal based on the location where they originate, or their timing relative to heart phase actions.)

Other non-worn sensors can also be employed, such as a weigh scale, camera, microphone, skin fold thickness calipers, sphygmomanometer, blood sugar sensor, etc. Some such sensors can be built into the user's household or office environment. For example, a weigh scale may be built into the floor in front of a bathroom sink, and a camera may be positioned to view the user's face when the user looks into a bathroom mirror.

Still other sensors may be applied to the body, e.g., adhesively or otherwise, for short intervals, as circumstances dictate. These include EEG and EKG electrodes, piezoelectric emitters/receptors, etc. Such localized sensors may be employed to track conditions at sites of particular concern, e.g., bruising or other wound, cancer site, etc. In some instances, sensors may be implanted.

All such sensing apparatus are desirably wirelessly linked, e.g., to convey data to a user's smartphone, to each other, or to a monitoring service.

When a user of an exemplary sensor network participates in a monitoring service, the logged parameters—or derivative information based thereon—are eventually sent to the cloud. The remote service monitors this data—noting and establishing time-of-day and day-of-week baselines, for different activity scenarios (e.g., sleep, office work, walking, strenuous exercising, etc., as classified based on characteristic collections of sensor data). These baselines can also be associated with different geographic locations, e.g., as determined by GPS or WiFi, or otherwise.

Such a monitoring service may report to the user whenever the sensed data significantly deviates from expected norms. If a person's REM sleep pulse is normally between 56 and 60 beats per second, and one night there is an episode in which the pulse varies from this range by a threshold amount (e.g., more than 5%, 15%, 30%, or 75%), then a message may be dispatched to the user (e.g., by email, text, or otherwise) noting the incident. Possible causes for the disturbance may also be communicated to the user. These causation hypotheses can be pro form a—based on textbook understandings of the noted phenomenon (e.g., caffeine before bed) discerned from stored rule data, or they can be tailored to the user—such as taking into account other user- or ambient-sensor information that might be correlated (e.g., irregular respiration, suggesting sleep apnea or the like; or an unusually warm room—as indicated by temperature data logged by a smartphone sensor as contrasted with historical norms—leading to increased blood flow for convective body cooling). Such information is also logged in a historical data store, and may also be sent for e-charting to the user's physician.

Part of a health and wellness protocol may involve the user speaking a particular phrase every day to an associated microphone sensor (e.g., "Good morning fitband"), for collection of baseline voice information. In some instances, an interactive dialog may ensue, with the system (e.g., the user's smartphone) consulting the user's available biometric signals and prompting—if appropriate—"You don't sound well" (in displayed or spoken text) and asking some follow-up questions, to help determine whether the user's malady is something that needs medical attention. Through such probing (which may proceed verbally, using speech recognition technology), the user may reveal that she was refinishing furniture yesterday evening with a powerful solvent, or was in a venue with lots of second hand smoke. Based on the collected sensor and verbal information, the system can consult stored knowledge base information in advising whether the user should consult medical personnel.

Another application of the present technology is in sleep analysis. Commercial sleep studies often involve instrumenting the patient with several different sensors, such as a band around the chest to sense respiratory effort; an O2 sensor on a finger; a sensor under the nose to detect smoothness of nasal flow; an accelerometer of the like to sense the vibration that commonly accompanies snoring, etc. All such information is sent to a data logging device. The collected information is eventually sent to a professional for analysis.

While such arrangement may be the gold standard for sleep analysis, much useful information can be derived from a much simpler setup, such as one employing sensors resident in a smartphone phone, and—if desired—accessory sensors that are wirelessly coupled to the smartphone. For example, vibration may be sensed by positioning the phone on the bed. Vibrations from the snoring will couple from the user to the bed, and then to the phone. (Vibratory amplitude will be diminished, and some dampening will occur, but useful information nonetheless results. These factors may be reversed, approximately, by signal processing, if desired.) Others of the parameters may be derived from analysis of captured audio. Again, human experience does not give the insight to discern the small clues evidencing respiratory effort, smoothness of nasal flow, etc. that are manifest in the sounds of snoring. But analysis of Big Data archives of such sounds—in conjunction with ground truth (e.g., captured from gold standard setups like the one just reviewed)—allows such clues to be sensed and properly interpreted.

Another application of the technology involves analysis of clicking and other noises from user joints (is that degenerative arthritis, or simple crepitus?). Still another involves stomach and bowel sounds (e.g., are those the little bowel tones associated with healthy peristalsis, or high tinkling sounds that may signal an obstruction?). Yet another involves sounds accompanying urine flow. Still another involves the sounds of blood turbulence when blood starts flowing following release in pressure from a blood pressure measurement cuff. Etc., etc. Again, lay humans typically don't discern much meaningful data from such sounds and their variations; many physicians don't do much better. But as collections of such sounds grow, and are complemented by ground truth interpretations by physicians, meaning emerges. The significant clues may not be evident in the raw audio; only by processing (e.g., by computing one or more of the features detailed in Table 1) may telling signals become apparent. But as the volume of reference data goes up, the meaning that can be derived goes up commensurately.

In many of the presently-detailed methods, historical user data is often the best baseline against which to judge current user data. However, statistical aggregates of large population groups also form useful comparison standards. For example, even without historical information, the system can advise a user that her sleeping respiration rate of 25 breaths per minute is experienced by persons of similar demographic profile only 1% of the time, and may merit professional attention.

As noted, each user's sensed information (or derived data) is desirably sent for storage in a cloud database service, which may aggregate data from thousands, or millions, of people. Just as fitness tracking watches (sometimes termed "activity loggers") have social network components (e.g., posting Facebook reports of the GPS route that users run in their daily jogs, with speed, distance traveled, calories, and heart rate, etc.), so too can a physiologic monitoring service. Default privacy settings can anonymize the uploaded data, but users may elect different settings—including to share selected categories of skin images, biometric information, activity status updates, etc., with network friends, without anonymization.

In some arrangements, the sensed data is associated with location information—both the location on the body from which it was collected, and also the geolocation at which the information was sensed (e.g., latitude and longitude). Data can then be recalled and analyzed, filtered, presented, etc., based on such location information. For example, a user can compare an average of resting pulse measurements taken at work, with such an average taken at home. Sensed information can also be presented in map form. For example, a user can query archived data to obtain a map display that identifies locations at which their resting pulse exceeded 80. (A suitable map display, detailing where certain data was sensed by a user, is illustrated in applicant's published patent application 20130324161.) Again, such information and maps can be shared via social networking services.

Historical user data serves as a statistical chronology of the user's aging process. Again, the user's physiologic signals can be compared to those of a relevant cohort (e.g., similarly-aged people of same gender, weight, location, etc.) to reflect whether the user is aging more or less rapidly than the norm. Relative aging may be judged by relative physiological condition.

Generally, aging is accompanied by phenomena including higher body weight, lower body height, higher BMI, lower lean body mass (muscle and bone mass), higher blood pressure (both systolic and diastolic), lower maximum oxygen use (VO2 max—Volume Maximum Oxygen consumption) under exertion (e.g., on a treadmill stress exam), decreased visual acuity (e.g., presbyopia—a lessening ability to focus on close objects), decreased hearing acuity, decreased skin tightness, etc.

Such phenomena can be sensed and used to assess physiological age, as contrasted with chronological age, in known fashion. In comparing a user's metrics with those of a relevant cohort, variance indicates the user is either physiologically younger, or older, than peers. This variance can be tracked over time. If a user is statistically judged to have a physiological age of 50 when actually 40, and later have a physiological age of 52 when actually 44, then the user is physiologically older than peers, but trending in a more healthful direction.

In similar fashion, trends of other biometric signals over time, e.g., compared with statistical norms, indicate the trajectory of a person's health.

As the collection of reference data and the collection of ground truth diagnostic information become larger, the frequency and/or range of errors associated with their use become smaller. At some point, such a system serves as a statistically reliable predictor of the future. A user may interact with a user interface of the system to propose certain changes (e.g., in diet, exercise, or other lifestyle) that might be made to avoid certain undesirable predicted outcomes, and the system can predict their respective effects.

Many apps are downloaded to users' phones, and left un-used after a week or so. In part, this is due to the hurdle of having to awaken the phone from sleep mode whenever use of the app is desired. Technologies are arising, however, (such as applicant's patent application 61/920,722, filed Dec. 24, 2013) in which portable user devices can maintain some functionality—such as audio responsiveness—even when "asleep." (In some embodiments, this capability relies on use of an auxiliary processor that is active all the time, and which consumes just a tiny fraction of the power consumed by the phone's primary processor(s).)

In accordance with another aspect of the technology, the audio and/or other physiologic signal sensing described herein is on-going even when the screen of the device is dark and the device is otherwise in a "sleep" mode. To reduce battery drain, the data collected in this mode is not streamed to the cloud, but rather is cached in a memory until the phone is next awakened. Similarly, the processing of the captured data to produce derivative data may be queued, e.g., waiting until the device's primary processor is again available. Thus, data collection aspects of a health app may be on-going, 24 hours a day, 7 days a week.

As noted, individual privacy is a concern with such technologies. Yet, so too is the importance of establishing a pool of shared information that is sufficiently large to bring benefits of scale and meaningful statistics. Users may sometimes serve as providers of their own information, and consumers of others' information. In such situation, there can be a marketplace for exchange of physiologic information. Those whose consumption is out of proportion to their sharing may be called on to pay, or offer other consideration, for their relatively high consumption (or, put another way, for their relatively heightened privacy). Those who share more than they consume may receive cash or other consideration to reward their relative openness. The marketplace can establish the equilibrium point between giving and taking, where no exchange of consideration is required.

(Some categories of information, e.g., carotid artery sounds, may be scarcer than others. Similarly, information from certain demographic segments, e.g., young women in North Dakota, may be scarcer than others. The exchange marketplace can take such factors into account in establishing pricing for information.)

In some arrangements, a person's consultation with a physician may not be prompted by use of the present technology; rather, a consultation with a physician may prompt use of the present technology.

For example, a patient may visit a physician prompted by an onset of wheezing in their respiration. On investigation, the physician may detect a murmur (which may be associated with the wheezing). The physician may instruct the patient to capture, twice-daily, sounds of the murmur by positioning the phone in a certain location on the chest. Such in-home data collection can then inform judgments by the physician about further care.

Similarly, a physician who diagnoses possible depression in a patient can use voice data from at-home data collection to determine whether the condition is trending better or worse. (The physician needn't review the actual recorded voice. Parameters expressing volume, pitch, and variations in same, can be derived from the patient's sensed voice, and succinctly reported for physician review.)

A hundred years ago, physicians didn't have labs that could analyze a bit of body fluid to produce a page full of quantitative data; they relied on their eyes, and ears, and their fingers. Lab data gives great insight into patient conditions, but something is lost when lab analysis replaces physical exam—as often now seems to be the case. Applications of the present technology redress this shortcoming, employing digital sensors that are more acute and accurate than any physician's senses. Coupled with insights from Big Data, digital sensor-assisted physical exam may again emerge as the primary tool of diagnostic medicine.

(As noted elsewhere—but it bears repeating, it is poor practice to make an automated diagnosis based on sensed data and statistics. But such information allows systems according to the present technology to conclude that something seems different or amiss, so that such fact can be revealed and acted on by a professional.)

Review

A very few of the novel arrangements detailed herein are reviewed in rough summary fashion, below.

One aspect of the present technology involves collecting physiologic information in a data structure, where the collected information corresponds to physiologic sensor data gathered by plural non-professional users. In the data structure is also collected professional evaluation information corresponding to at least some of the physiologic information. Thereafter, query information is received, corresponding to physiologic sensor data gathered by a non-professional user. The data structure is consulted in determining result information, and at least some of this result information is communicated to the non-professional user. This result information depends on correlation between the query information, the collected physiology information, and the professional evaluation information.

Another arrangement employs a portable device that is moved to plural different viewpoint positions relative to a skin location. At a first of these viewpoint positions, the skin location is illuminated with light of a first spectrum from the portable device. While so-illuminated, imagery of the skin location is captured using a camera in the portable device. At a second of these viewpoint positions, the skin location is illuminated with light of a second spectrum from the portable device. Again, while so-illuminated, imagery of the skin location is captured using the portable device. Thus, the skin location is imaged by the portable device from plural different viewpoint positions and with plural different illumination spectra. The captured imagery may then be processed and, based on such processing, the user may be advised whether to seek a professional evaluation of the skin location.

In a related method, the skin location is illuminated with light of a first spectrum from a first region of a display of the portable device, while imagery of the skin location is captured. Similarly, the skin location is illuminated with light of a second spectrum from a second region of the portable device display. Again, imagery of the skin location is captured while illuminated with this second spectrum of light. By such arrangement, imagery of the skin location is captured with plural different illumination angles and plural different illumination spectra.

Still another related method involves presenting a first illumination from a portable device display screen to a subject at a first time, and capturing a first image of the subject when it is so-illuminated. Likewise, second illumination is presented from the display screen to the subject at a second time, and a second image of the subject, so-illuminated, is captured. In such arrangement, the illumination does not comprise a viewfinder rendering of captured imagery.

Another aspect of the technology involves capturing image information from a reference subject, using a camera, and processing the captured image information to yield reference color information. Imagery is also captured with the camera, depicting a skin rash or lesion. This latter imagery is then color-corrected by use of the reference color information. (The reference subject can comprise, e.g., blood or a banknote.)

Still another aspect of the technology involves receiving imagery comprising plural frames depicting a skin rash or lesion. A processing operation is invoked on the plural frames, to yield an enhanced still image (e.g., (a) a super-resolution image, (b) a noise-reduced image, (c) a multi-spectral image, (d) an ambient light-compensated image, or (e) a 3D image). The enhanced still image (or data derived therefrom) is submitted to a database for similarity-matching with reference images depicting skin rashes or lesions, or data derived from such reference images. Such database includes reference data corresponding to enhanced still images that themselves have been processed from plural-frame imagery.

Yet another arrangement according to the present technology involves obtaining plural sets of professional data, where each set includes skin image data and patient profile data. This patient profile data includes both opinion information provided by a medical professional, and factual information. From the skin image data, first feature information is extracted (e.g., using a hardware processor configured to perform such act). Plural sets of lay data are also obtained, where this lay data includes skin image data and patient profile data (e.g., fact data), but lacks information provided by a medical professional. From the skin image data in the lay data, second feature information is extracted. The first and second extracted feature information is then made available as reference feature information for similarity-matching with feature information extracted from query skin image data.

Still another aspect of the technology involves receiving data, including skin image data and associated metadata, from a party. Similarities between the received data and reference data are determined. This reference data includes multiple sets of data, each including skin image data and associated metadata. Included among the reference data are sets of data that have been professionally curated, and also sets of data that have not been professionally curated.

A further method involves receiving a first set of information from a first submitter, where the first set of information includes imagery depicting a part of a first subject's body that evidences a symptom of a first pathological condition, and also includes drug profile data indicating drugs taken by the first subject. A second set of information is received from a second submitter. This second set of information includes imagery depicting a part of a second subject's body that evidences a symptom of a second pathological condition, and also includes drug profile data indicating drugs taken by the second subject. Such sets of information are received from 3d through Nth submitters. Information is then received corresponding to a query image submitted by a user. One or more image parameters are computed from this query image, and compared for correspondence against such parameters computed for the imagery received from the first through Nth submitters. Information is then sent to the user, identifying one or more drugs that is correlated with skin imagery (e.g., skin symptoms) having an appearance like that in the query image.

Yet another method involves receiving a first set of information from a first submitter, where this first set of information includes imagery depicting a part of a first subject's body that evidences a symptom of a first pathological condition, and also includes a diagnosis of the first pathological condition. Such information is likewise received from a second submitter, including imagery depicting part of a second subject's body that evidences a symptom of a second pathological condition, and also includes a diagnosis of the second pathological condition. This is repeated for third through Nth sets of information, received from third through Nth submitters. Information is then received corresponding to a query image submitted by a user. One or more parameters are computed from the query image. A search is conducted to identify imagery received from the first through Nth submitters having correspondence with the computed image parameter(s). Information (e.g., information about candidate diagnoses, or about diagnoses that are inconsistent with the available information) are then sent to the user, based on such searching of imagery.

Still another method involves obtaining first imagery depicting a part of a mammalian body that evidences a symptom of a possible pathological condition. This imagery is processed to derive one or more image parameter(s). A data structure is searched for reference information, based on the derived image parameter(s). Result information is determined as a consequence of such search. This reference information comprises information identifying one or more particular pathological conditions that is not the pathological condition evidenced by the depicted part of the body. At least some of this result information is communication to a user.

A further aspect of the technology involves sensing whether a mobile device is in a static, viewing pose. When it is not, frames of imagery depicting a user are collected. When it is in the static viewing pose, information is presented for user review. This presented information is based, at least in part, on the collected frames of imagery. In such arrangement, the mobile device automatically switches between data collection and data presentation modes (e.g., based on pose and/or motion).

A further aspect of the technology involves capturing audio sounds from a user's body, using a portable device held by the user. Plural features are derived from the captured audio; these features comprise fingerprint information corresponding to the captured sounds. This fingerprint information is provided to a knowledge base (data structure), which contains reference fingerprint data and associated metadata. Metadata associated with one or more of the reference fingerprint data in the knowledge base is then received back by the device. Information based on this received metadata (e.g., physiologic- or health-related information) is presented to the user.

Still another aspect of the present technology concerns an imaging booth defined by one or more sidewalls. A plurality of cameras are disposed along the one or more side walls, directed toward an interior of the booth, and these cameras are connected to an image processor. The booth also includes a plurality of light sources directed toward the interior of the booth, coupled to driving electronics. Plural of these light sources is each spectrally tuned to a different wavelength, and the driving electronics are adapted so that different of the lighting elements illuminate at different times, causing the cameras to capture imagery under plural different spectral lighting conditions. The image processor is adapted to produce spectricity measurements based on imagery from the cameras.

CONCLUDING REMARKS

Having described and illustrated the principles of the inventive work with reference to illustrative examples, it will be recognized that the technology is not so limited.

For example, medical diagnosis often relies heavily on patient history. Such history information can be extracted from medical records, and used in assessing the possible diagnostic relevance of different physiologic signals, or combinations of signals.

To illustrate, crackles or rales in the lungs, for most people, may indicate pneumonia—even if accompanied by a gain in weight. However, if these symptoms appear in a person known to be suffering from chronic heart failure, then the lung sounds take on a new significance—one that requires a prompt visit to the doctor.

Likewise, DNA testing is becoming more commonplace. A physiologic signal (e.g., crackles or rales) may take on new meaning when interpreted in the context of particular DNA findings (which may indicate, e.g., a susceptibility to particular viral illnesses).

Although the focus of this disclosure has been on capture of imagery, audio, and more familiar physiologic data, mention should also be made of haptics. Haptic technology allows data to be acquired concerning tactile information—such as the firmness, tautness, elasticity or resilience of a body part. (See, e.g., Murayama, et al, Development of a New Instrument for Examination of Stiffness in the Breast Using Haptic Sensor Technology, Sensors and Actuators A: Physical 143.2, pp. 430-438, 2008.) In addition to haptic sensors, haptic actuators can also be employed—applying physical forces to the body in controlled direction, strength, and temporal pattern, so that measurement data responsive to such stimulus can be sensed. Again, by collection of a body of haptic information, and correlation with physicians' diagnostic ground truth, certain haptic data (or its derivatives) can be discovered to have diagnostic significance.

While the Face-Chek mode noted above employed rainbow mode illumination, it will be recognized that the Face-Chek mode can also use other lighting arrangements, e.g., simple ambient light.

Certain of the described arrangements may capture imagery in which the body of the camera device (e.g., smartphone) casts a visible shadow. Arrangements for detailing with such shadows are detailed in applicant's U.S. Pat. No. 8,488,900.

While one of the above-detailed dermatological embodiments employed a brute force, exhaustive search through a knowledge base to assess similarities with reference image data, more sophisticated methods can naturally be employed.

One is to provide indices to the database, sorted by different parameters. Thus in the case of a simple scalar parameter that ranges from 0-100, if the query image has a parameter of 37, then a binary or other optimized search can be conducted in the index to quickly identify reference images with similar parameter values. Reference images with remote values needn't be considered for this parameter. (Most of the detailed image derivatives are vector parameters, comprising multiple components. Similar database optimization methods can be applied.)

Still further, known machine learning techniques can be applied to the reference data to discern which image derivatives are most useful as diagnostic discriminants of different conditions. When a query image is received, it can be tested for these discriminant parameters to more quickly perform a Bayesian evaluation of different candidate diagnosis hypotheses.

Bag-of-features techniques (sometimes termed "bag of words" techniques) can also be mployed to ease, somewhat, the image matching operation (but such techniques "cheat" by resort to data quantization that may—in some instances—bias the results). Other pattern recognition techniques developed for automated mole diagnosis can likewise be adapted to identifying database images that are similar to a query image.

Certain embodiments of the present technology can employ existing online catalogs of imagery depicting different dermatological symptoms and associated diagnoses. Examples include DermAtlas, at www<dot>dermatlas<dot>org—a crowd-sourced effort managed by physicians at Johns Hopkins University) and DermNet NZ at www<dot>dermnetnz<dot>org—a similar effort by the New Zealand Dermatological Society. Similarly-named to the latter is Dermnet, a skin disease atlas organized by a physician in New Hampshire, based on submittals from various academic institutions, www<dot>dermnet<dot>com. Also related is the website Differential Diagnosis in Dermatology, www<dot>dderm<dot>blogspot<dot>com, and the web site of the International Dermoscopy Society, www<dot>dermoscopy-ids<dot>org.

Sometimes patient privacy rights (e.g., HIPAA) pose an impediment to collection of imagery, even for anonymous, crowd-source applications. As suggested above, one approach to collection of crowd-sourced imagery is to offer financial incentives to patients to induce them to share their mole imagery or other physiologic information.

While one of the detailed arrangements presented a ranked listing of possible pathologies to consider (or to rule out), other embodiments can present information otherwise, e.g., with other representations of confidence. Histograms, heat maps, and phylogenetic diagrams are examples.

In some embodiments, the technology serves as an advisor to a medical professional—offering suggested diagnoses, or further testing, to consider. The offered advice may be tailored in accordance with wishes of the professional, e.g., expressed in stored profile data corresponding to that professional. For example, one practitioner may express a conservative medical philosophy, in which case such an advisory service may offer only observations/suggestions in which there is a high degree of confidence. Conversely, another practitioner may be more open to novel theories and approaches, in which case the system may also present candidate diagnoses (and further testing suggestions) that is more speculative.

Similarly, some practitioners may specify diagnostic criteria that they tend to weigh more (or less) heavily in reaching particular conclusions. In dermatology, for instance, one physician may regard chromatic diversity across a mole as particularly relevant to a diagnosis of malignant melanoma. Another physician may not hold such criterion in high regard, but may find scalloped edge contours to be highly probative for such a diagnosis. Again, stored profile data for the different professionals can indicate such preferences, and tailor system response accordingly. (In some arrangements, such preferences are not expressly specified as profile information by the physician, but rather are deduced through analysis of electronic medical records detailing previous diagnoses, and the clinical data on which they were based.)

In processing imagery, e.g., of moles, known photogrammetry techniques are desirably employed to mitigate for pose distortion and camera optics, to yield an orthorectified image (aka an orthoimage). So doing enhances the statistical matching of user-submitted skin imagery with previously-submitted imagery.

While the skin conditions discussed above are organic in nature, the same principles can be applied to skin conditions that result from trauma, including bug bites and wounds. A user who returns from a vacation with a painful leg bite may wonder: Is it a spider bite? A flea? A bed bug? A scrape that doesn't heal well, and turns red and angry, may be another cause for concern: Is that a staph infection? As in the cases detailed above, a suitably-large knowledge base can reveal answers.

Reference was made to sensed information, and other information derived therefrom. This latter information is variously referred to in this specification, e.g., as features, parameters, fingerprints, derived data, etc. It should be understood that these latter terms are interchangeable.

Another form of metadata that may be associated with sensed user data (e.g., skin images) is information indicating treatments the user has tried, and their assessment of success (e.g., on a 0-10 scale). In the aggregate, such data may reveal effective treatments for different types of rashes, acne, etc.

Skin also serves as a barometer of other conditions, including emotion. Each emotion activates a different collection of bodily systems, triggering a variety of bodily responses, e.g., increased blood flow (vasocongestion) to different regions, sometimes in distinctive patterns that can be sensed to infer emotion. (See, e.g., Nummenmaa, et al, Bodily Maps of Emotions, Proceedings of the National Academy of Sciences of the United States of America, 111, pp. 646-651, 2014.) Just as skin conductivity is used in some lie detectors, so too may skin imagery.

In some systems, sensed physiologic information and its derivatives are represented in the form of Linked Data—both for individual and aggregate data, and both for storage and for sharing—in order to facilitate semantic reasoning with such information. (The artisan is presumed to be familiar with Linked Data and related constructs, e.g., as popularized by Tim Berners-Lee, as standardized by the World Wide Web Consortium, and as discussed in the assignee's patent publications including 20110098056 and 20120154633.)

In other embodiments, imagery, image derivatives, and metadata information are stored in accordance with the DICOM standards for medical image records (see, e.g., www<dot>dclunie<dot>com/dicom-status/status<dot>html).

Certain embodiments of the technology recognize the user's forearm or other body member (e.g., by classification methods), and use this information in later processing (e.g., in assessing scale of skin features). In some such arrangements, analysis is applied to video information captured while the user is moving the smartphone camera into position to capture skin imagery. Such "flyover" video is commonly of lower resolution, and may suffer from some blurring, but is adequate for body member-recognition purposes. If, e.g., a hand is recognized from one or more frames of such video, and the smartphone is thereafter moved (as sensed by accelerometers and/or gyroscopes) in a manner consistent with that hand being the ultimate target for imaging (e.g., the smartphone is moved in a direction perpendicular to the plane of the phone screen—moving it closer to the hand), then the subject of the image is known to be the hand, even if the captured diagnostic image itself is a close-up from which the body location cannot be deduced.

Many of the techniques described in connection with humans can also be applied to animals. Unusual skin conditions can be expanded to animal hide, fur and feathers (although false positives and hidden conditions may be more likely with complex skin coverings). Vets often face a more difficult challenge than physicians, since animals cannot describe symptoms that might aid in diagnosis, making the notion of providing a candidate list of maladies and being able to quickly test for additional symptoms even more valuable. Pet owners often need to decide whether symptoms warrant a visit to a vet and whether particular visible symptoms can be explained by recent known activities of that pet. Furthermore, livestock owners face the challenge of outbreaks of contagious diseases and need to inspect their animals often to catch such diseases as early as possible. Pet and livestock owners can benefit greatly from the present technology for examining and diagnosing conditions.

For livestock owners, an automated early warning system can be set in place where livestock passing through gates or paddocks are routinely examined for unusual skin variations that suggest closer examination is needed. Livestock are often outfitted with RF tags for identification, allowing such a monitoring system to compare individual livestock over time to rule out health conditions that have already been addressed, and to note new, emerging conditions. Wildlife managers can also benefit by setting up imaging systems on commonly traversed paths that are triggered by passing animals. Again, early detection and identification of contagious conditions or dangerous pests is key to maintaining healthy populations.

Another diagnostically useful feature is temporal observation of blood flow through the area of a skin condition. Subtle color changes due to local blood pressure modulated by heartbeats can be used to distinguish between, or assess the severity of, some skin conditions. One method of observing these subtle color changes is given in the Wu paper cited below ("Eulerian Video Magnification for Revealing Subtle Changes in the World"), where small differences are magnified through spatio-temporal signal processing. Elasticity of a region can be measured by applying pressure (by machine or by touch) in such a way as to bend the skin. By comparing various points on the skin before and after deformation (ideally, a repeated pattern of deformation to allow for averaging), the local elastic properties of the skin can be included in the diagnosis.

While 3D considerations were noted above (e.g., in regard to structure-from-motion methods), the local 3D texture of the skin condition region can also be assessed through the use of 3D imaging technology, including light-field and plenoptic cameras. One can consider both the angle of illumination of the incident light with respect to the imaging sensor as well as a lens cluster that provides depth variations as a byproduct of the imaging method.

Image analysis in the Lab color space is often preferred to RGB-based analysis, since normal skin color is a relatively small region in (a,b). The value of L (luminance) depends on the concentration of melanin, the skin color dye.

Reference was made to surface topology, and methods regarding same. Accurate 3D information can also be obtained from a single camera system by illuminating a region of interest of the patient with a structured light pattern. Distortions in the structured light pattern are used to determine the 3D structure of the region, in familiar manner. The pattern may be projected, e.g., by a projector associated with the camera system. (E.g., a mobile phone or headworn apparatus can include a pico data projector.)

Another group of image processing techniques useful in diagnostic analyses is Mathematical Morphology (see, e.g., the Wikipedia article of that name), where the topology of an image is described in terms of spatial surface descriptions. This is used, e.g., in counting of small creatures/structures under a microscope. Such technology is well suited to counting "bumps" or other structures per area in a skin lesion. It also allows for representation by attributed relational graphs that describe a detailed relationship between structures that can be compared as graphs independent of orientation and specific configuration.

It will be recognized that the term "lesion" is used in this specification in a generic sense, e.g., referring to any feature of the skin, including spots, moles, rashes, nevi, etc.

While reference was made to app software on a user's smartphone as performing certain of the detailed functionality, in other embodiments these functions can naturally be performed otherwise—including by operating system software on a smartphone, by a remote server, by another smartphone or computer device, distributed between such devices, etc.

While reference has been made to smartphones, it will be recognized that this technology finds utility with all manner of devices—both portable and fixed. Tablets, laptop computers, digital cameras, wrist- and head-mounted systems and other wearable devices, servers, etc., can all make use of the principles detailed herein. (The term "smartphone" should be construed herein to encompass all such devices, even those that are not telephones.)

Reference was made to "bag of features" techniques. Such methods extract local features from patches of an image (e.g., SIFT points), and automatically cluster the features into N groups (e.g., 168 groups)—each corresponding to a prototypical local feature. A vector of occurrence counts of each of the groups (i.e., a histogram) is then determined, and serves as a reference signature for the image, or for a sub-part thereof. To determine if a query image matches the reference image, local features are again extracted from patches of the image, and assigned to one of the earlier-defined N-groups (e.g., based on a distance measure from the corresponding prototypical local features). A vector occurrence count is again made, and checked for correlation with the reference signature. Further information is detailed, e.g., in Nowak, et al, Sampling strategies for bag-of-features image classification, Computer Vision—ECCV 2006, Springer Berlin Heidelberg, pp. 490-503; and Fei-Fei et al, A Bayesian Hierarchical Model for Learning Natural Scene Categories, IEEE Conference on Computer Vision and Pattern Recognition, 2005; and references cited in such papers. Some of applicant's related work, e.g., concerning imaging, image processing systems, and related smartphone apps is detailed in patent publications 20110212717, 20110161076, 20120284012, 20120046071, 20140052555, 20130329006, 20140057676, and in pending application Ser. No. 13/842,282, filed Mar. 15, 2013 (published as 20140198240), Ser. No. 14/251,229, filed Apr. 11, 2014 (published as 20150016712), 61/861,931, filed Aug. 2, 2013, and Ser. No. 13/969,422, filed Aug. 16, 2013 (published as 20140071268).

Several references have been made to application Ser. No. 14/201,852. In addition to extensive disclosure of several multi-spectral imaging techniques, that document teaches a variety of other arrangements that are useful in conjunction with the present technology. These include techniques for mitigating errors in spectricity measurements, compensation for field angle non-uniformities, various classification methods (including vector quantization, support vector machines, and neural network techniques), different object recognition technologies, and image comparison based on the freckle transform data, among others.

SIFT is an acronym for Scale-Invariant Feature Transform, a computer vision technology pioneered by David Lowe and described in various of his papers including "Distinctive Image Features from Scale-Invariant Keypoints," International Journal of Computer Vision, 60, 2 (2004), pp. 91-110; and "Object Recognition from Local Scale-Invariant Features," International Conference on Computer Vision, Corfu, Greece (September 1999), pp. 1150-1157, as well as in U.S. Pat. No. 6,711,293. Additional information about SIFT (and similar techniques SURF and ORB) is provided in the patent documents cited herein.

While SIFT is referenced, other robust feature points may be preferred for skin imagery. For example, SIFT is typically performed on grey-scale imagery; color is ignored. In contrast, feature points for skin can advantageously employ color. An exemplary set of feature points specific to close-up skin imagery can comprise skin pores (or hair follicles). The center of mass of each such feature is determined, and the pixel coordinates of each are then associated with the feature in a data structure. In other arrangements, 3D features can additionally or alternatively be used. Features can also be drawn from those that are revealed by infrared sensing, e.g., features in the dermal layer, including blood vessel minutiae. (See, e.g., Seal, et al, Automated Thermal Face Recognition Based on Minutiae Extraction, Int. J. Computational Intelligence Studies, 2013, 2, 133-156, attached to application 61/872,494, and references cited therein.)

The design of smartphones and other such devices reference herein is familiar to the artisan. In general terms, each includes one or more processors, one or more memories (e.g. RAM), storage (e.g., a disk or flash memory), a user interface (which may include, e.g., a keypad, a TFT LCD or OLED display screen, touch or other gesture sensors, a camera or other optical sensor, a compass sensor, a 3D magnetometer, a 3-axis accelerometer, a 3-axis gyroscope, one or more microphones, etc., together with software instructions for providing a graphical user interface), interconnections between these elements (e.g., buses), and an interface for communicating with other devices (which may be wireless, such as GSM, 3G, 4G, CDMA, WiFi, WiMax, Zigbee or Bluetooth, and/or wired, such as through an Ethernet local area network, a T-1 internet connection, etc.).

The processes and system components detailed in this specification can be implemented as instructions for computing devices, including general purpose processor instructions for a variety of programmable processors, including microprocessors (e.g., the Intel Atom, the ARM A5, and the Qualcomm Snapdragon, and the nVidia Tegra 4; the latter includes a CPU, a GPU, and nVidia's Chimera computational photography architecture), graphics processing units (GPUs, such as the nVidia Tegra APX 2600, and the Adreno 330—part of the Qualcomm Snapdragon processor), and digital signal processors (e.g., the Texas Instruments TMS320 and OMAP series devices), etc. These instructions may be implemented as software, firmware, etc. These instructions can also be implemented in various forms of processor circuitry, including programmable logic devices, field programmable gate arrays (e.g., the Xilinx Virtex series devices), field programmable object arrays, and application specific circuits—including digital, analog and mixed analog/digital circuitry. Execution of the instructions can be distributed among processors and/or made parallel across processors within a device or across a network of devices. Processing of signal data may also be distributed among different processor and memory devices. "Cloud" computing resources can be used as well. References to "processors," "modules" or "components" should be understood to refer to functionality, rather than requiring a particular form of implementation.

Software instructions for implementing the detailed functionality can be authored by artisans without undue experimentation from the descriptions provided herein, e.g., written in C, C++, Visual Basic, Java, Python, Tcl, Perl, Scheme, Ruby, etc. Smartphones and other devices according to certain implementations of the present technology can include software modules for performing the different functions and acts.

Software and hardware configuration data/instructions are commonly stored as instructions in one or more data structures conveyed by tangible media, such as magnetic or optical discs, memory cards, ROM, etc., which may be accessed across a network. Some embodiments may be implemented as embedded systems—special purpose computer systems in which operating system software and application software are indistinguishable to the user (e.g., as is commonly the case in basic cell phones). The functionality detailed in this specification can be implemented in operating system software, application software and/or as embedded system software.

The databases and other data structures referenced herein can be monolithic, or can be distributed. Thus, reference data may be stored anywhere, e.g., user devices, remote device, in the cloud, divided between plural locations, etc.

While the specification described certain acts as being performed by the user device (phone) or by the central system, it will be recognized that any processor can usually perform any function. For example, computation of image derivatives, and color correction, can be done by the user's smartphone or by the central system—or distributed between various devices. Thus, the fact that an operation is described as being performed by one apparatus, should be understood as exemplary and not limiting.

In like fashion, description of data being stored on a particular device is also exemplary; data can be stored anywhere: local device, remote device, in the cloud, distributed, etc.

As indicated, the present technology can be used in connection with wearable computing systems, including headworn devices. Such devices typically include one or more sensors (e.g., microphone(s), camera(s), accelerometers(s), etc.), and display technology by which computer information can be viewed by the user—either overlaid on the scene in front of the user (sometimes termed augmented reality), or blocking that scene (sometimes termed virtual reality), or simply in the user's peripheral vision. A headworn device may further include sensors for detecting electrical or magnetic activity from or near the face and scalp, such as EEG and EMG, and myoelectric signals—sometimes termed Brain Computer Interfaces, or BCIs. (A simple example of a BCI is the Mindwave Mobile product by NeuroSky, Inc.) Exemplary wearable technology is detailed in U.S. Pat. No. 7,397,607, 20100045869, 20090322671, 20090244097 and 20050195128. Commercial offerings, in addition to the Google Glass product, include the Vuzix Smart Glasses M100, Wrap 1200AR, and Star 1200XL systems. An upcoming alternative is augmented reality contact lenses. Such technology is detailed, e.g., in patent document 20090189830 and in Parviz, Augmented Reality in a Contact Lens, IEEE Spectrum, September, 2009. Some or all such devices may communicate, e.g., wirelessly, with other computing devices (carried by the user or otherwise), or they can include self-contained processing capability. Likewise, they may incorporate other features known from existing smart phones and patent documents, including electronic compass, accelerometers, gyroscopes, camera(s), projector(s), GPS, etc.

As noted, embodiments of present technology can also employ neuromorphic processing techniques (sometimes termed "machine learning," "deep learning," or "neural network technology"). As is familiar to artisans, such techniques employ large arrays of artificial neurons—interconnected to mimic biological synapses. These methods employ programming that is different than the traditional, von Neumann, model. In particular, connections between the circuit elements are weighted according to correlations in data that the processor has previously learned (or been taught).

Each artificial neuron, whether physically implemented or simulated in a computer program, receives a plurality of inputs and produces a single output which is calculated using a nonlinear activation function (such as the hyperbolic tangent) of a weighted sum of the neuron's inputs. The neurons within an artificial neural network (ANN) are interconnected in a topology chosen by the designer for the specific application. In one common topology, known as a feed-forward network, the ANN consists of an ordered sequence of layers, each containing a plurality of neurons. The neurons in the first, or input, layer have their inputs connected to the problem data, which can consist of image or other sensor data, or processed versions of such data. Outputs of the first layer are connected to the inputs of the second layer, with each first layer neuron's output normally connected to a plurality of neurons in the second layer. This pattern repeats, with the outputs of one layer connected to the inputs of the next layer. The final, or output, layer produces the ANN output. A common application of ANNs is classification of the input signal into one of N classes (e.g., classifying a type of mole). In this case the output layer may consist of N neurons in one-to-one correspondence with the classes to be identified. Feed-forward ANNs are commonly used, but feedback arrangements are also possible, where the output of one layer is connected to the same or to previous layers.

Associated with each connection within the ANN is a weight, which is used by the input neuron in calculating the weighted sum of its inputs. The learning (or training) process is embodied in these weights, which are not chosen directly by the ANN designer, In general, this learning process involves determining the set of connection weights in the network that optimizes the output of the ANN is some respect. Two main types of learning, supervised and unsupervised, involve using a training algorithm to repeatedly present input data from a training set to the ANN and adjust the connection weights accordingly. In supervised learning, the training set includes the desired ANN outputs corresponding to each input data instance, while training sets for unsupervised learning contain only input data. In a third type of learning, called reinforcement learning, the ANN adapts on-line as it is used in an application. Combinations of learning types can be used; in feed-forward ANNs, a popular approach is to first use unsupervised learning for the input and interior layers and then use supervised learning to train the weights in the output layer.

When a pattern of multi-dimensional data is applied to the input of a trained ANN, each neuron of the input layer processes a different weighted sum of the input data. Correspondingly, certain neurons within the input layer may spike (with a high output level), while others may remain relatively idle. This processed version of the input signal propagates similarly through the rest of the network, with the activity level of internal neurons of the network dependent on the weighted activity levels of predecessor neurons. Finally, the output neurons present activity levels indicative of the task the ANN was trained for, e.g. pattern recognition. Artisans will be familiar with the tradeoffs associated with different ANN topologies, types of learning, and specific learning algorithms, and can apply these tradeoffs to the present technology.

Another machine learning arrangement that is well suited for embodiments of the present technology is support vector machines (SVMs). SVMs are detailed, e.g., in U.S. Pat. Nos. 6,157,921, 6,714,925, 7,797,257 and 8,543,519.

Additional information on such techniques is detailed in the Wikipedia articles on "Machine Learning," "Deep Learning," and "Neural Network Technology," as well as in Le et al, Building High-Level Features Using Large Scale Unsupervised Learning, arXiv preprint arXiv:1112.6209 (2011), and Coates et al, Deep Learning with COTS HPC Systems, Proceedings of the 30th International Conference on Machine Learning (ICML-13), 2013. These journal papers, and then-current versions of the "Machine Learning" and "Neural Network Technology" articles, are attached as appendices to copending patent application 61/861,931, filed Aug. 2, 2013. Application Ser. No. 14/201,852 also has a discussion of machine learning useful with the present technology.

Reference was made to statistical findings based on the reference data. The artisan is presumed to be familiar with statistics and their use.

In some of the foregoing examples, reference was made to a condition being statistically unlikely or improbable. The particular threshold used in such determinations can be set by the implementer, based on the requirements of the particular application. In some arrangements, a probability of less than 1% may be deemed statistically unlikely. In others, a probability of less than 0.3%, 0.1%, 0.03% or 0.01% may be required.

Pulse detection from wearable clothing and devices is taught, e.g., in U.S. Pat. Nos. 5,622,180, 6,104,947 and 7,324,841 to Polar Electro OY.

Other related writings include U.S. Pat. Nos. 6,021,344, 6,606,628, 6,882,990, 7,233,693, 20020021828, 20080194928, 20110301441, 2012008838, 20120308086, and WO13070895, and the following other publications (all appended to application 61/832,715):

Arafini, "Dermatological disease diagnosis using color-skin images," 2012 Intl Conf on Machine Learning and Cybernetics;

Bersha, "Spectral Imaging and Analysis of Human Skin," Master's Thesis, University of Eastern Finland, 2010;

Cavalcanti, et al, "An ICA-based method for the segmentation of pigmented skin lesions in macroscopic images, IEEE Int'l Conf on Engineering in Medicine and Biology Society, 2011;

Cavalcanti, et al, Macroscopic pigmented skin lesion segmentation and its influence on lesion classification and diagnosis, Color Medical Image Analysis. Springer Netherlands, 2013, pp. 15-39;

Korotkov et al, "Computerized analysis of pigmented skin lesions—a review," Artificial Intelligence in Medicine 56, pp. 69-90 (2012);

Parolin, et al, "Semi-automated diagnosis of melanoma through the analysis of dermatological images," 2010 23rd IEEE SIBGRAPI Conference on Graphics, Patterns and Images;

Sadeghi et al, "Detection and analysis of irregular streams in dermoscopic images of skin lesions," preprint, IEEE Trans. on Medical Imaging, 2013;

Sadeghi, et al, "Automated Detection and Analysis of Dermoscopic Structures on Dermoscopy Images," 22nd World Congress of Dermatology, 2011; and Wu, Eulerian Video Magnification for Revealing Subtle Changes in the World, ACM Transactions on Graphics, Vol. 31, No. 4 (2012) p 65 (8 pp.).

Other related writings include the following, each appended to application 61/872,494:

Abbas, et al, Hair Removal Methods: a Comparative Study for Dermoscopy Images, Biomedical Signal Processing and Control 6.4, 2011, pp. 395-404;

Armstrong et al, Crowdsourcing for Research Data Collection in Rosacea, Dermatology Online Journal, Vol. 18, No. 3, March, 2012;

Baeg et al, Organic Light Detectors—Photodiodes and Phototransistors Advanced Materials, Volume 25, Issue 31, Aug. 21, 2013;

Bellazzi, et al, Predictive Data Mining in Clinical Medicine—Current Issues and Guidelines, Int'l J. of Medical Informatics, V. 77, 2008, pp. 81-97;

BioGames—A Platform for Crowd-Sourced Biomedical Image Analysis and Telediagnosis, Games Health, Oct. 1, 2012, pp. 373-376;

Cruz, et al, Applications of Machine Learning in Cancer Prediction and Prognosis, Cancer Infom., No. 2, 2006, pp. 59-77;

Csurka, et al, Visual Categorization with Bags of Keypoints, ECCV, Workshop on Statistical Learning in Computer Vision, 2004;

Dalal, et al, Histograms of Oriented Gradients for Human Detection, IEEE Conference on Computer Vision and Pattern Recognition, pp. 886-893, 2005;

di Leo, Automatic Diagnosis of Melanoma: A Software System Based on the 7-Point Check-List, Proc. 43d Hawaii Int'l Conf. on System Sciences, 2010;

Foncubierta-Rodriguez et al, Ground Truth Generation in Medical Imaging, Proc. of the ACM Multimedia 2012 workshop on Crowdsourcing for Multimedia, pp. 9-14;

Fuketa, et al, Large-Area and Flexible Sensors with Organic Transistors, 5th IEEE Int'l Workshop on Advances in Sensors and Interfaces, 2013;

Jacobs et al, Focal Stack Compositing for Depth of Field Control, Stanford Computer Graphics Laboratory Technical Report 2012-1;

Johnson, et al, Retrographic Sensing for the Measurement of Surface Texture and Shape, 2009 IEEE Conf. on Computer Vision and Pattern Recognition;

Kaliyadan, Teledermatology Update—Mobile Teledermatology, World Journal of Dermatology, May 2, 2013, pp. 11-15;

Liu, et al, Incorporating Clinical Metadata with Digital Image Features for Automated Identification of Cutaneous Melanoma, pre-print from British Journal of Dermatology, Jul. 31, 2013;

Lyons, et al, Automatic classification of single facial images, IEEE Trans. on Pattern Analysis and Machine Intelligence, Vol. 21, No. 12, 1999, pp. 1357-1362;

Parsons, et al, Noninvasive Diagnostic Techniques for the Detection of Skin Cancers, in Comparative Effectiveness Technical Briefs, No. 11, US Agency for Healthcare Research and Quality, September, 2011;

Seal, et al, Automated Thermal Face Recognition Based on Minutiae Extraction, Int. J. Computational Intelligence Studies, 2013, No. 2, 133-156;

Vellido, et al, Neural Networks and Other Machine Learning Methods in Cancer Research, in Computational and Ambient Intelligence, Springer, 2007, pp. 964-971;

Wadhawan, et al, SkinScan: A Portable Library for Melanoma Detection on Handheld Devices, Proc. IEEE Int'l Symp. on Biomedical Imaging, Mar. 30, 2011, pp. 133-136;

Wolf et al, Diagnostic Inaccuracy of Smartphone Applications for Melanoma Detection, JAMA Dermatology, Vol. 149, No. 4, April 2013; and Zeng, et al, Colour and Tolerance of Preferred Skin Colours, Color and Imaging Conference, Society for Imaging Science and Technology, 2010.

The artisan is presumed to be familiar with such art.

This specification details a variety of arrangements. It should be understood that the methods, elements and concepts detailed in connection with one arrangement can be combined with the methods, elements and concepts detailed in connection with other embodiments. (For example, methods, principles and arrangements described in connection with imagery can be applied in connection with audio, etc., and vice versa. Similarly, polarized light can be used advantageously in embodiments employing SLAM or SFM techniques, and in detecting robust feature points. Etc.) Likewise with features from the cited references. While some such arrangements have been particularly described, many have not—due to the large number of permutations and combinations. However, implementation of all such combinations is straightforward to the artisan from the provided teachings.

While this disclosure has detailed particular ordering of acts and particular combinations of elements, it will be recognized that other contemplated methods may re-order acts (possibly omitting some and adding others), and other contemplated combinations may omit some elements and add others, etc.

Although disclosed as complete systems, sub-combinations of the detailed arrangements are also separately contemplated (e.g., omitting various features of a complete system).

While certain aspects of the technology have been described by reference to illustrative methods, it will be recognized that apparatuses configured to perform the acts of such methods are also contemplated as part of applicant's inventive work. Likewise, other aspects have been described by reference to illustrative apparatus, and the methodology performed by such apparatus is likewise within the scope of the present technology. Still further, tangible computer readable media containing instructions for configuring a processor or other programmable system to perform such methods is also expressly contemplated.

The present specification should be read in the context of the cited references. (The reader is presumed to be familiar with such prior work.) Those references disclose technologies and teachings that applicant intends be incorporated into embodiments of the present technology, and into which the technologies and teachings detailed herein be incorporated.

To provide a comprehensive disclosure, while complying with the statutory requirement of conciseness, applicant incorporates-by-reference each of the documents referenced herein. (Such materials are incorporated in their entireties, even if cited above in connection with specific of their teachings. For example, while patent publication 20110301441 was referenced in connection with purpose-built imaging hardware, other technologies disclosed in that publication can also be used advantageously herein.)

In view of the wide variety of embodiments to which the principles and features discussed above can be applied, it should be apparent that the detailed embodiments are illustrative only, and should not be taken as limiting the scope of the technology. Rather, applicant claims all such modifications as may come within the scope and spirit of the attached claims and equivalents thereof.

The invention claimed is:

1. A method comprising:
   receiving first imagery depicting a part of a mammalian body that evidences a symptom of a possible pathological condition;
   processing the received imagery to derive one or more image parameter(s);
   searching a data structure for reference information, based on the derived image parameter(s);
   from the reference information, determining result information, said determining including identifying one or more particular pathological conditions that is inconsistent with the pathological condition evidenced by said depicted part of the body; and
   reporting, to a user, a name of at least one of said identified pathological conditions that is inconsistent with the pathological condition evidenced by said depicted part of the body.

2. The method of claim 1 in which the first imagery depicts said part of the body at a first time, and the method further includes:
   receiving second imagery depicting said part of the body at a second time, later than the first time;
   determining data about a change in said symptom between the first and second times, based on said first and second imagery; and
   using said determined data in said identifying the one or more particular pathological conditions that is not the pathological condition evidenced by said depicted part of the body.

3. The method of claim 1 in which the processing comprises one or more of: determining, or performing, a color histogram, a blob analysis, and a frequency domain transformation.

4. The method of claim 1 in which the reference information includes multiple sets of reference data, each corresponding to a reported diagnosis of a pathological condition in a reference subject, and each including reference image-based information.

5. The method of claim 4 that further includes identifying plural candidate pathological conditions consistent with said received first imagery, and presenting a listing of said conditions to the user, ranked by probability.

6. A method comprising:
   receiving first imagery depicting a part of a mammalian body that evidences a symptom of a possible pathological condition;
   processing the received imagery to derive one or more image parameter(s);
   searching a data structure for reference information, based on the derived image parameter(s), the reference information including multiple sets of reference data, each corresponding to a reported diagnosis of a pathological condition in a reference subject, and each including reference image-based information;

from the reference information, determining result information, said determining including identifying one or more particular pathological conditions that is inconsistent with the pathological condition evidenced by said depicted part of the body; and communicating at least some of the result information to a user, said communicating including identifying to the user at least one particular pathological condition that is inconsistent with the pathological condition evidenced by said depicted part of the body; and also identifying plural candidate pathological conditions that are consistent with said received first imagery, and presenting a listing of said candidate conditions to the user, ranked by probability;

wherein plural of said sets of reference data each includes drug profile data indicating one or more drug(s) taken by said respective reference subject, and the method includes:

identifying a drug most commonly associated with one of said candidate pathological conditions; and reporting said identified drug to the user as a further clue to diagnosis.

7. The method of claim 1 in which the mammalian body is a non-human body.

8. The method of claim 1 in which the first imagery includes a known object distinct from the body, and the processing includes determining a camera pose relative to the body based on apparent geometrical distortion of the object in said imagery, and applying a corrective counter-distortion to the first imagery to account for said apparent geometrical distortion.

9. A non-transitory computer readable medium containing software instructions operable to configure a system to perform acts including:

receiving first imagery, the first imagery depicting a part of a mammalian body that evidences a symptom of a possible pathological condition;

processing the received imagery to derive one or more image parameter(s);

submitting a query to a data structure based on the derived image parameter(s), and receiving reference information in response;

from the reference information, determining result information, said determining including identifying one or more particular pathological conditions that is inconsistent with the pathological condition evidenced by said depicted part of the body; and reporting, to a user, a name of at least one of said identified pathological conditions that is inconsistent with the pathological condition evidenced by said depicted part of the body.

* * * * *